(12) United States Patent
Akahane et al.

(10) Patent No.: US 10,456,023 B2
(45) Date of Patent: Oct. 29, 2019

(54) IMAGE SENSOR, ENDOSCOPE, AND ENDOSCOPE SYSTEM

(71) Applicant: OLYMPUS CORPORATION, Tokyo (JP)

(72) Inventors: Nana Akahane, Yamanashi (JP); Satoru Adachi, Tsuchiura (JP); Takanori Tanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/940,089

(22) Filed: Mar. 29, 2018

(65) Prior Publication Data

US 2018/0220880 A1  Aug. 9, 2018

Related U.S. Application Data

(63) Continuation of application No. PCT/JP2016/079352, filed on Oct. 3, 2016.

(30) Foreign Application Priority Data

Oct. 2, 2015 (JP) .................. 2015-196784

(51) Int. Cl.
*A61B 1/05* (2006.01)
*A61B 1/04* (2006.01)
(Continued)

(52) U.S. Cl.
CPC .......... *A61B 1/051* (2013.01); *A61B 1/00009* (2013.01); *A61B 1/04* (2013.01);
(Continued)

(58) Field of Classification Search
CPC .................................................... A61B 1/051
See application file for complete search history.

(56) References Cited

U.S. PATENT DOCUMENTS 8,933,413 B2  1/2015  Kitano et al.
9,137,472 B2  9/2015  Minagawa et al.
(Continued)

FOREIGN PATENT DOCUMENTS

JP  2012-151596 A  8/2012
JP  2013-055500 A  3/2013
(Continued)

OTHER PUBLICATIONS

International Search Report dated Nov. 8, 2016 issued in PCT/JP2016/079352.

*Primary Examiner* — James M Pontius
(74) *Attorney, Agent, or Firm* — Scully, Scott, Murphy & Presser, P.C.

(57) ABSTRACT

An image sensor includes: pixels; first transfer lines configured to transfer imaging signals of shared pixels that are present in a plurality of different rows and share a single column transfer line for each predetermined number of pixels adjacent in a row direction and; a constant current source configured to transfer the imaging signals; output units configured to externally output the imaging signals; and a control unit configured to simultaneously and externally outputs, by simultaneously driving the plurality of shared pixels present in a same single column transfer line in the plurality of different rows, each of the plurality of imaging signals, which are output from the shared pixels and are present in the same column in the plurality of different rows, and externally output all of the imaging signals of the shared pixels present in the plurality of different rows same number of times as the predetermined number.

8 Claims, 10 Drawing Sheets

(51) Int. Cl.

| | | |
|---|---|---|
| *H04N 5/3745* | (2011.01) | |
| *H04N 5/378* | (2011.01) | |
| *H04N 7/18* | (2006.01) | |
| *A61B 1/00* | (2006.01) | |
| *A61B 1/045* | (2006.01) | |
| *H04N 5/225* | (2006.01) | |
| *H04N 5/357* | (2011.01) | |
| *H04N 5/232* | (2006.01) | |
| *H04N 5/345* | (2011.01) | |

(52) U.S. Cl.
CPC ........... *A61B 1/045* (2013.01); *H04N 5/2256* (2013.01); *H04N 5/23203* (2013.01); *H04N 5/345* (2013.01); *H04N 5/357* (2013.01); *H04N 5/3575* (2013.01); *H04N 5/378* (2013.01); *H04N 5/3745* (2013.01); *H04N 5/37457* (2013.01); *H04N 7/18* (2013.01); *H04N 2005/2255* (2013.01)

(56) References Cited

U.S. PATENT DOCUMENTS

| | | | |
|---|---|---|---|
| 9,769,409 | B2 | 9/2017 | Minagawa et al. |
| 2008/0001861 | A1* | 1/2008 | Asano ............... G09G 3/2014 345/77 |
| 2010/0271522 | A1* | 10/2010 | Matsunaga .......... H04N 5/2176 348/302 |
| 2012/0182455 | A1 | 7/2012 | Gomi et al. |
| 2013/0057744 | A1 | 3/2013 | Minagawa et al. |
| 2013/0140467 | A1 | 6/2013 | Kitano et al. |
| 2013/0141618 | A1 | 6/2013 | Kobayashi |
| 2014/0293105 | A1* | 10/2014 | Sugawa ............. H04N 5/37457 348/304 |
| 2015/0085980 | A1 | 3/2015 | Kitano et al. |
| 2016/0057372 | A1* | 2/2016 | Iwane ............... H04N 5/37457 348/300 |
| 2017/0318252 | A1 | 11/2017 | Minagawa et al. |
| 2018/0054580 | A1* | 2/2018 | Adachi ................ H04N 5/363 |
| 2018/0064314 | A1* | 3/2018 | Adachi ............. A61B 1/00096 |

FOREIGN PATENT DOCUMENTS

| | | |
|---|---|---|
| JP | 2013-118501 A | 6/2013 |
| WO | WO 2007/108129 A1 | 9/2007 |
| WO | WO 2012/008229 A1 | 1/2012 |

\* cited by examiner

IMAGE SENSOR, ENDOSCOPE, AND ENDOSCOPE SYSTEM

CROSS-REFERENCE TO RELATED APPLICATION

This application is a continuation of PCT International Application No. PCT/JP2016/079352 filed on Oct. 3, 2016 which claims the benefit of priority from Japanese Patent Application No. 2015-196784, filed on Oct. 2, 2015, the entire contents of which are incorporated herein by reference.

BACKGROUND

The present disclosure relates to an image sensor, an endoscope, and an endoscope system.

In recent years, regarding complementary metal oxide semiconductor (CMOS) image sensors, there is a known technology for allowing a plurality of adjacent pixels to share a single vertical signal line and transferring image signals (see International Publication Pamphlet No. WO 2007/108129). With this technology, by allowing a plurality of adjacent pixels to share a single vertical signal line, a small sized image sensor with high pixel is implemented.

SUMMARY

An image sensor according to one aspect of the present disclosure includes: a plurality of pixels arranged in a two-dimensional matrix and configured to receive light from outside and generate imaging signals in accordance with an amount of received light; a plurality of first transfer lines configured to transfer the imaging signals of shared pixels that are present in a plurality of different rows and share a single column transfer line for each predetermined number of pixels adjacent in a row direction and; a constant current source provided in each of the plurality of first transfer lines and configured to transfer the imaging signals output from the pixels to the first transfer lines; a plurality of output units configured to externally output the imaging signals transferred from the plurality of first transfer lines; and a control unit configured to simultaneously and externally outputs, from the plurality of output units, by simultaneously driving the plurality of shared pixels present in a same single column transfer line in the plurality of different rows, each of the plurality of imaging signals, which are output from the shared pixels and are present in the same column in the plurality of different rows, and externally output all of the imaging signals of the shared pixels present in the plurality of different rows same number of times as the predetermined number.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
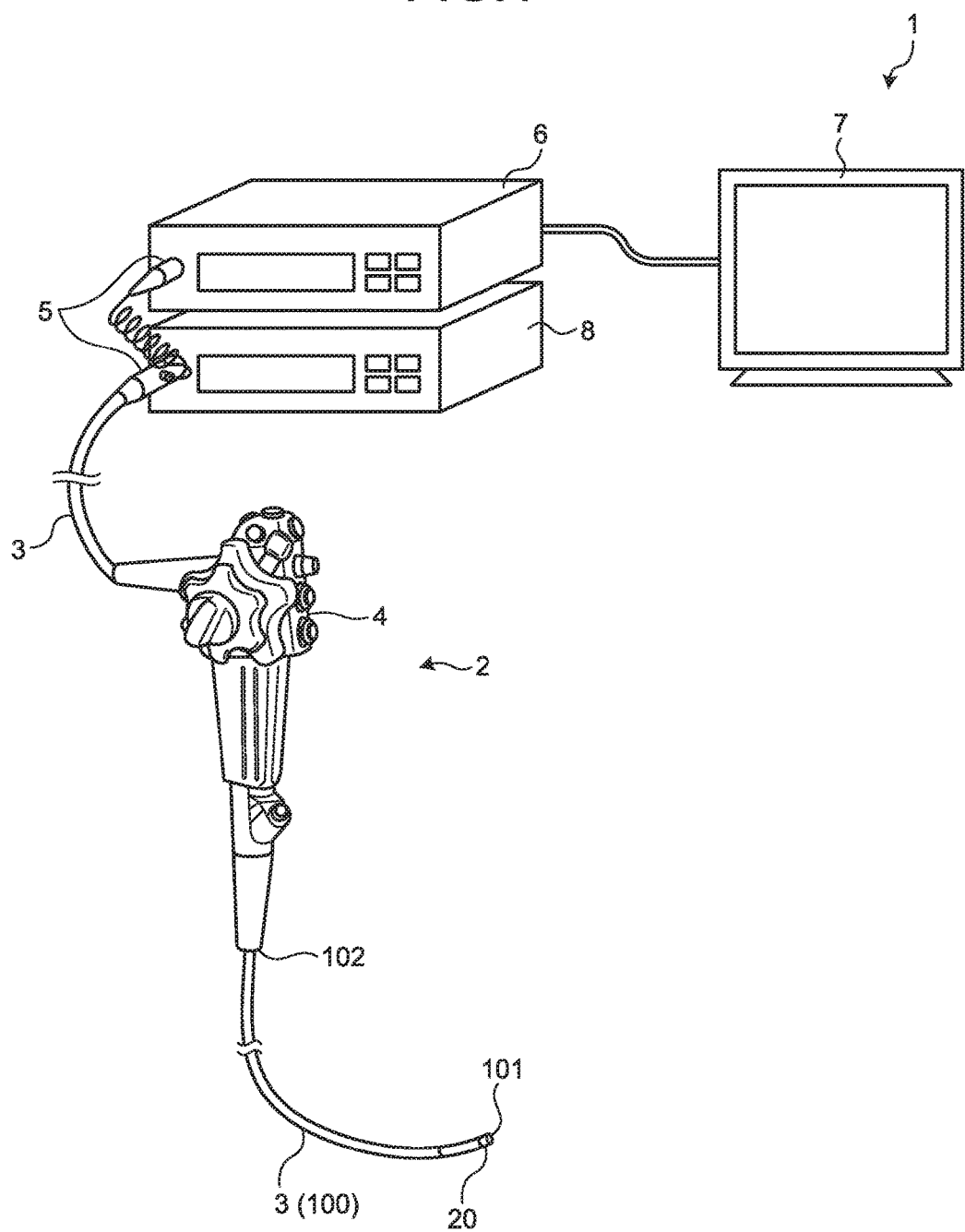
FIG. 1 is a schematic diagram illustrating the overall configuration of an endoscope system according to a first embodiment.

In the following, as modes for carrying out the present disclosure (hereinafter, referred to as "embodiments"), an endoscope system provided with an endoscope having image sensor that is disposed at a distal end of an insertion portion that is inserted into a subject will be described. The present disclosure is not limited to the embodiments. In the drawings, components that are identical to those in embodiments are assigned the same reference numerals. The drawings used for the descriptions below are only schematic illustrations. The relationship between the thickness and the width of each member, the proportions of each member, and so on are different from those used in practice. The size or reduction in scale of elements may sometimes differ between the drawings.

First Embodiment

Configuration of Endoscope System

FIG. 1 is a schematic diagram illustrating the overall configuration of an endoscope system according to a first embodiment. An endoscope system 1 illustrated in FIG. 1 includes an endoscope 2, a transmission cable 3, a connector portion 5, a processor 6 (processing device), a display device 7, and a light source device 8.

The endoscope 2 captures an image of the interior of a subject by inserting an insertion portion 100 that is a part of the transmission cable 3 into a body cavity of the subject and then outputs an imaging signal (image data) to the processor 6. Furthermore, in the endoscope 2, an imaging unit 20 (imaging device) that captures an in-vivo image is provided at a distal end 101 side, which is one end of the transmission cable 3, of the insertion portion 100 that is inserted into the body cavity of the subject and an operating unit 4 that receives various operations performed with respect to the endoscope 2 is provided on a proximal end 102 side of the insertion portion 100. The imaging signal of the image captured by the imaging unit 20 passes through the transmission cable 3 having a length of, for example, several meters and is output to the connector portion 5.

The transmission cable 3 connects the endoscope 2 and the connector portion 5 and connects the endoscope 2 and the light source device 8. Furthermore, the transmission cable 3 propagates the imaging signal generated by the imaging unit 20 to the connector portion 5. The transmission cable 3 is formed by using a cable, an optical fiber, or the like.

The connector portion 5 is connected to the endoscope 2, the processor 6, and the light source device 8; performs predetermined signal processing on the imaging signal that is output by the connected endoscope 2; converts an analog imaging signal to a digital imaging signal (A/D conversion); and outputs the converted imaging signal to the processor 6.

The processor 6 performs predetermined image processing on the imaging signal that is input from the connector portion 5 and then outputs the processed imaging signal to the display device 7. Furthermore, the processor 6 performs overall control of the endoscope system 1. For example, the processor 6 performs control for changing the illumination light emitted by the light source device 8 and switching an imaging mode of the endoscope 2.

The display device 7 displays an image associated with the imaging signal that has been subjected to image processing by the processor 6. Furthermore, the display device 7 displays various kinds of information related to the endoscope system 1. The display device 7 is formed by using a display panel, such as a liquid crystal or organic electro luminescence (EL) display panel.

The light source device 8 irradiates an object with illumination light from the distal end 101 side of the insertion portion 100 of the endoscope 2 via the connector portion 5 and the transmission cable 3. The light source device 8 is formed by using a white light emitting diode (LED) that emits white light, an LED that emits special light of narrow-band light having a wavelength band narrower than the wavelength band of the white light. The light source device 8 irradiates, under the control of the processor 6, the object with the white light or the narrow-band light via the endoscope 2.

Figure 2:
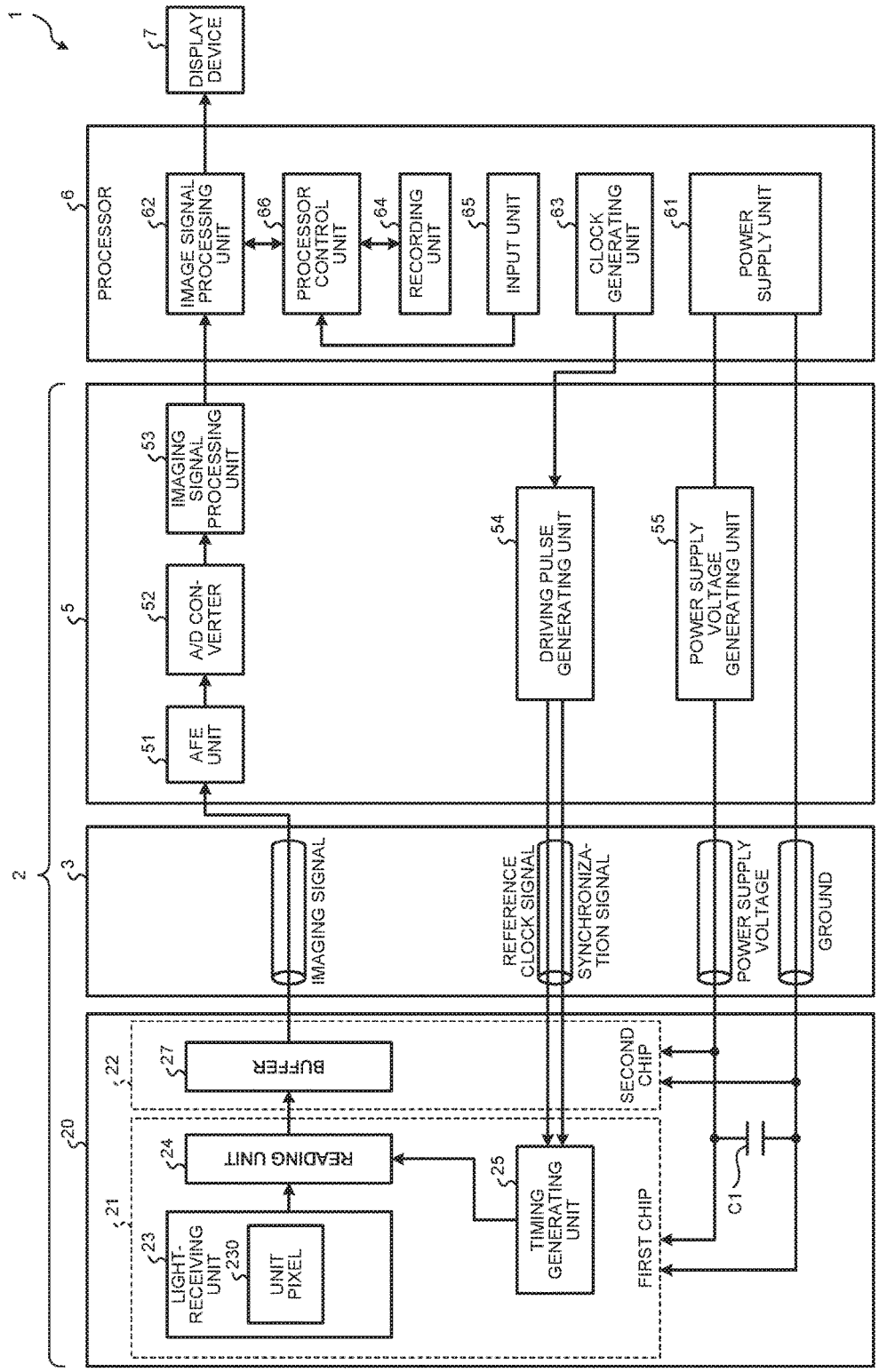
FIG. 2 is a block diagram illustrating a function of a relevant part of the endoscope system illustrated in FIG. 1.

FIG. 2 is a block diagram illustrating a function of a relevant part of the endoscope system 1 illustrated in FIG. 1. Each of the components in the endoscope system 1 in detail and the path of the electrical signal in the endoscope system 1 will be described with reference to FIG. 2.

Configuration of Endoscope

First, the configuration of the endoscope 2 will be described. The endoscope 2 illustrated in FIG. 2 includes the imaging unit 20, the transmission cable 3, and the connector portion 5.

The imaging unit 20 includes a first chip 21 (image sensor) and a second chip 22. Furthermore, the imaging unit 20 receives, together with ground GND, a power supply voltage VDD generated by a power supply voltage generating unit 55, which will be described later, in the connector portion 5 via the transmission cable 3. A condenser C1 used to stabilize a power supply is provided between the power supply voltage VDD supplied to the imaging unit 20 and the ground GND.

The first chip 21 includes a light-receiving unit 23 having a plurality of arrayed unit pixels 230 that are arranged in a two-dimensional matrix, that receive light from outside, that generate image signals in accordance with an amount of light received, and that output the generated image signals; a reading unit 24 that reads an imaging signal subjected to photoelectric conversion in each of the unit pixels 230 in the light-receiving unit 23; and a timing generating unit 25 that generates a timing signal based on the reference clock signal and a synchronization signal input from the connector portion 5 and that outputs the generated signals to the reading unit 24. A more detailed description of the configuration of the first chip 21 will be described later.

The second chip 22 includes a buffer 27 that amplifies the imaging signal output from each of the unit pixels 230 in the first chip 21 and that outputs the amplified imaging signals to the transmission cable 3. Furthermore, a combination of the circuits disposed on the first chip 21 and the second chip 22 may appropriately be changed. For example, the timing generating unit 25 disposed on the first chip 21 may also be disposed on the second chip 22.

The connector portion 5 includes an analog front-end unit 51 (hereinafter, referred to as an "AFE unit 51"), an A/D converter 52, an imaging signal processing unit 53, a driving pulse generating unit 54, and the power supply voltage generating unit 55.

The AFE unit 51 receives the imaging signals propagated from the imaging unit 20; extracts an alternating-current component by using the condenser after having performed impedance matching by using a passive element, such as a resistance; and determines an operating point based on partial pressure resistance. Then, the AFE unit 51 corrects the imaging signals (analog signals) and outputs the corrected imaging signals to the A/D converter 52.

The A/D converter 52 converts the analog imaging signals input from the AFE unit 51 to digital imaging signals and outputs the converted signals to the imaging signal processing unit 53.

The imaging signal processing unit 53 is formed by, for example, a field programmable gate array (FPGA), performs a process, such as noise removal and format conversion processes, on the digital imaging signals that are input from the A/D converter 52, and then outputs the processed signal to the processor 6.

The driving pulse generating unit 54 generates, based on a reference clock signal (for example, a clock signal with 27 MHz) that is supplied from the processor 6 and that is the criteria for the operation of each of the components in the endoscope 2, a synchronization signal indicating a start position of each frame and outputs the generated synchronization signal, together with the reference clock signal, to the timing generating unit 25 in the imaging unit 20 via the transmission cable 3. Here, the synchronization signal generated by the driving pulse generating unit 54 includes horizontal synchronization signals and vertical synchronization signals.

The power supply voltage generating unit 55 generates a power supply voltage needed to drive the first chip 21 and the second chip 22 from the power supply supplied from the processor 6 and then outputs the generated power supply voltage to the first chip 21 and the second chip 22. The power supply voltage generating unit 55 generates the power supply voltage needed to drive the first chip 21 and the second chip 22 by using a regulator or the like.

Configuration of Processor

In the following, the configuration of the processor 6 will be described. The processor 6 is a control device that performs overall control of the endoscope system 1. The processor 6 includes a power supply unit 61, an image signal processing unit 62, a clock generating unit 63, a recording unit 64, an input unit 65, and a processor control unit 66.

The power supply unit 61 generates a power supply voltage VDD and supplies the generated power supply voltage VDD to, together with the ground (GND), the power supply voltage generating unit 55 in the connector portion 5.

The image signal processing unit 62 converts a digital imaging signal subjected to signal processing by the imaging signal processing unit 53 to an image signal by performing image processing, such as a synchronization process, a white balance (WB) adjustment process, a gain adjustment process, a gamma correction process, a digital analog (D/A) conversion process, a format conversion process, and then outputs the processed image signal to the display device 7.

The clock generating unit 63 generates a reference clock signal that is the criteria for the operation of each of the components in the endoscope system 1 and outputs the reference clock signal to the driving pulse generating unit 54.

The recording unit 64 records various kinds of information related to the endoscope system 1 and data that is being processed. The recording unit 64 is formed by using a recording medium, such as a flash memory or a random access memory (RAM).

The input unit 65 receives various operations related to the endoscope system 1. For example, the input unit 65 receives an input of an instruction signal that switches the type of the illumination light emitted by the light source device 8. The input unit 65 is formed by using, for example, a cross switch or a push button.

The processor control unit 66 performs overall control of the units that form the endoscope system 1. The processor control unit 66 is formed by using a central processing unit (CPU). The processor control unit 66 switches, in accordance with the instruction signal input from the input unit 65, the illumination light emitted by the light source device 8.

Configuration of the First Chip

Figure 3:
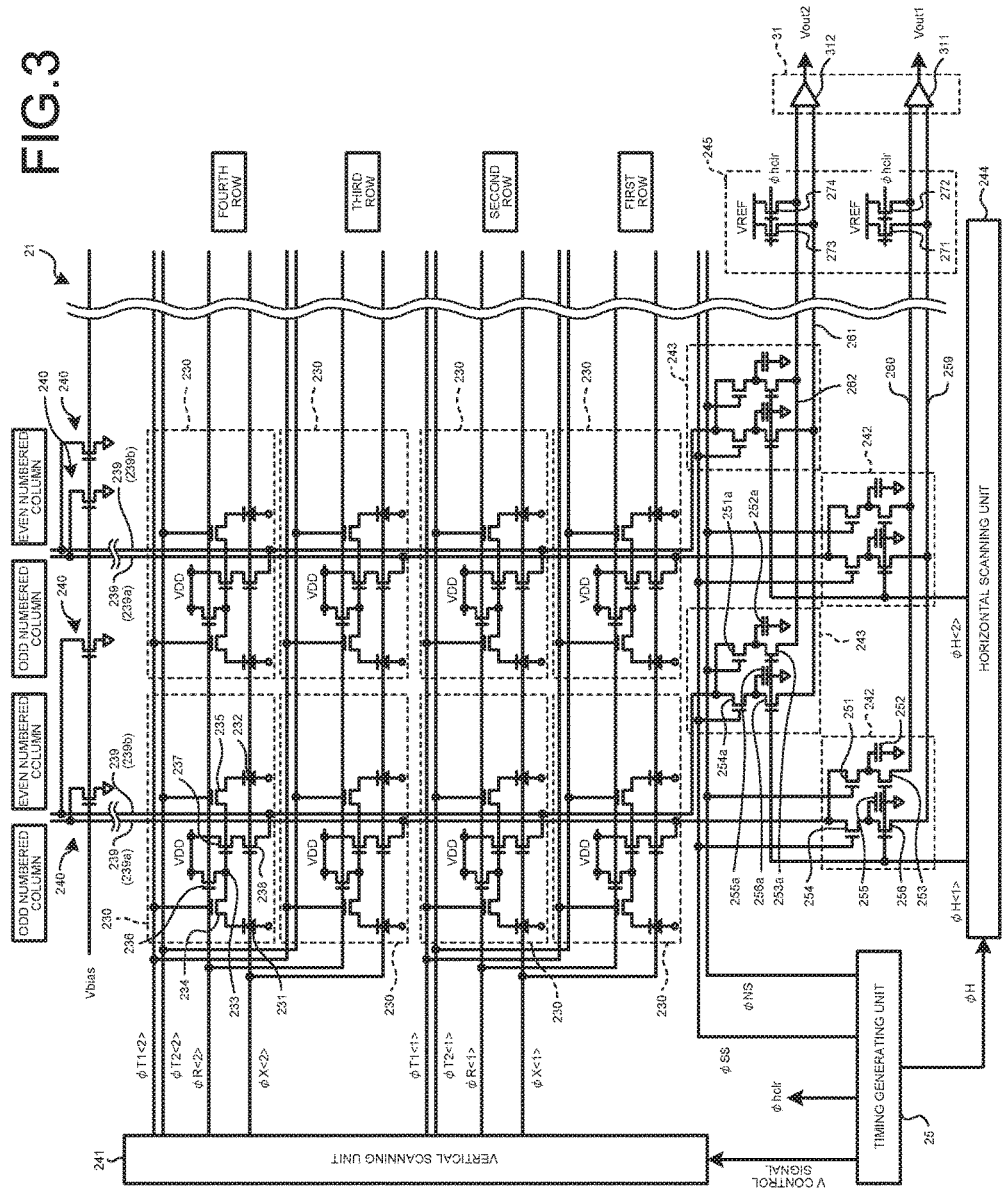
FIG. 3 is a circuit diagram illustrating the configuration of a first chip illustrated in FIG. 2.

In the following, a detailed configuration of the above described first chip 21 will be described. FIG. 3 is a circuit diagram illustrating the configuration of the first chip 21 illustrated in FIG. 2. As illustrated in FIG. 3, the first chip 21 includes the timing generating unit 25, an output unit 31, constant current sources 240, a vertical scanning unit 241 (row selection circuit), first sample hold units 242, second sample hold units 243, a horizontal scanning unit 244 (column selection circuit), and a horizontal reset unit 245.

The timing generating unit 25 generates, based on the reference clock signal and the synchronization signal, various driving pulses (V control signal, $\phi$hclr, $\phi$SS, $\phi$NS, and $\phi$H) and outputs the driving pulses to each of the vertical scanning unit 241, the first sample hold units 242, the horizontal scanning unit 244, and the horizontal reset unit 245, which will be described later. The timing generating unit 25 simultaneously and externally outputs, by simultaneously driving the unit pixels 230 present in a plurality of rows adjacent in the vertical direction (column direction), each of the plurality of imaging signals that are output from the unit pixels 230 in the plurality of rows. In the first embodiment, the timing generating unit 25 functions as a control unit.

One end of the constant current source 240 is connected to the ground GND and the other end thereof is connected to a vertical transfer line 239 and a signal line to which a reference voltage Vbias is input is connected to the gate.

The vertical scanning unit 241 applies, based on the driving pulses ($\phi$X, $\phi$R, $\phi$T1, $\phi$T2, and the like) input from the timing generating unit 25, each of a row selection pulse $\phi$X<M>, a driving pulse $\phi$R<M>, a driving pulse $\phi$T1<M>, and a driving pulse $\phi$T2<M> to the selected rows <M> (M=1, 2, . . . , and m) in the light-receiving unit 23 and drives each of the unit pixels 230 in the light-receiving unit 23 by the constant current sources 240 that are connected to the vertical transfer lines 239, whereby the vertical scanning unit 241 transfers, by using the vertical transfer lines 239 (first transfer lines), the imaging signals and noise signals at the time of pixel reset and then outputs each of the noise signals and the imaging signals to the first sample hold units 242. In the first embodiment, the imaging signals are read from two unit pixels 230 in a shared manner.

Each of the first sample hold units 242 (sample hold circuit) samples the noise signals at the time of pixel reset in each of the unit pixels 230 in the odd numbered rows and outputs the sampled noise signals to the output unit 31. Furthermore, each of the first sample hold units 242 samples the imaging signals subjected to photoelectric conversion in each of the unit pixels 230 in the odd numbered rows and outputs the sampled imaging signals to the output unit 31. Each of the first sample hold units 242 includes a first sampling switch 251, a first sampling unit 252 (capacitor), a first output switch 253, a second sampling switch 254, a second sampling unit 255, and a second output switch 256.

One end of the first sampling switch 251 is connected to the vertical transfer line 239 (239*a*), the other end thereof is connected to one end of the first output switch 253, and a signal line to which the driving pulse $\phi$NS is input from the timing generating unit 25 is connected to the gate.

One end of the first sampling unit 252 is connected between the first sampling switch 251 and the first output switch 253 and the other end thereof is connected to the ground GND. Each of the first sampling units 252 samples (holds) the noise signals received from the unit pixels 230, in the case where the row selection pulse $\phi$X<M> and the driving pulse $\phi$R<M> are applied to the unit pixels 230, when the driving pulse $\phi$NS is applied to the gate of each of the first sampling switches 251.

One end of the first output switch 253 is connected to the first sampling switch 251, the other end thereof is connected to a second horizontal transfer line 260, and a column selection pulse $\phi$H<M> is input to the gate from the horizontal scanning unit 244. When the column selection pulse $\phi$H<M> is applied to the gate, the first output switch 253 transfers the noise signals sampled by the first sampling unit 252 to the second horizontal transfer line 260.

One end of the second sampling switch 254 is connected to the vertical transfer line 239 (239*a*), the other end thereof is connected to one end of the second output switch 256, and a signal line to which the driving pulse $\phi$SS is input from the timing generating unit 25 is connected to the gate.

One end of the second sampling unit 255 is connected between the second sampling switch 254 and the second output switch 256 and the other end thereof is connected to the ground GND. The second sampling unit 255 samples (holds) the imaging signals received from the unit pixels 230, in the case where the row selection pulse $\phi$X<M> and the driving pulse $\phi$T1<M> or the driving pulse $\phi$T2<M> are applied to the unit pixels 230, when the driving pulse $\phi$SS is applied to the gate of the second sampling switch 254.

One end of the second output switch 256 is connected to the second sampling switch 254, the other end thereof is connected to a first horizontal transfer line 259, and the column selection pulse $\phi$H<M> is input to the gate from the horizontal scanning unit 244. When the column selection pulse $\phi$H<M> is applied to the gate, the second output switch 256 transfers the imaging signals sampled by the second sampling unit 255 to the first horizontal transfer line 259.

The second sample hold units 243 (sample hold circuit) have the same configuration as those of the first sample hold units 242, sample the noise signals at the time of pixel reset in each of the unit pixels 230 in the even numbered rows, and output the sampled noise signals to the output unit 31. Furthermore, the second sample hold units 243 sample the imaging signals subjected to photoelectric conversion in each of the unit pixels 230 in the even numbered rows and output the sampled imaging signals to the output unit 31. Each of the second sample hold units 243 includes a first sampling switch 251*a*, a first sampling unit 252*a* (capacitor), a first output switch 253*a*, a second sampling switch 254*a*, a second sampling unit 255*a*, and a second output switch 256*a*.

One end of the first sampling switch 251*a* is connected to the vertical transfer line 239 (239*b*), the other end thereof is connected to one end of the first output switch 253*a*, a signal line to which the driving pulse ϕNS is input from the timing generating unit 25 is connected to the gate.

One end of the first sampling unit 252*a* is connected between the first sampling switch 251*a* and the first output switch 253*a* and the other end thereof is connected to the ground GND. The first sampling unit 252*a* samples (holds) the noise signals received from the unit pixels 230, in the case where the row selection pulse ϕX<M> and the driving pulse ϕR<M> are applied to the unit pixels 230, when the driving pulse ϕNS is applied to the gate of the first sampling switch 251*a*.

One end of the first output switch 253*a* is connected to the first sampling switch 251*a*, the other end thereof is connected to a fourth horizontal transfer line 262, and the column selection pulse ϕH<M> is input to the gate from the horizontal scanning unit 244. If the column selection pulse ϕH<M> is applied to the gate, the first output switch 253*a* transfers the noise signals sampled by the first sampling unit 252*a* to the fourth horizontal transfer line 262.

One end of the second sampling switch 254*a* is connected to the vertical transfer line 239 (239*b*), the other end thereof is connected to one end of the second output switch 256*a*, a signal line to which the driving pulse ϕSS is input from the timing generating unit 25 is connected to the gate.

One end of the second sampling unit 255*a* is connected between the second sampling switch 254*a* and the second output switch 256*a* and the other end thereof is connected to the ground GND. The second sampling unit 255*a* samples (holds) the imaging signals received from the unit pixels 230, in the case where the row selection pulse ϕX<M> and the driving pulse ϕT1<M> or the driving pulse ϕT2<M> are applied to the unit pixels 230, when the driving pulse ϕSS is applied to the gate of the second sampling switch 254*a*.

One end of the second output switch 256*a* is connected to the second sampling switch 254*a*, the other end thereof is connected to a third horizontal transfer line 261, and the column selection pulse ϕH<M> is input to the gate from the horizontal scanning unit 244. When the column selection pulse ϕH<M> is applied to the gate, the second output switch 256*a* transfers the imaging signals sampled by the second sampling unit 255*a* to the third horizontal transfer line 261.

The horizontal scanning unit 244 applies, based on the driving pulse (ϕH) supplied from the timing generating unit 25, the column selection pulse ϕH<M> to the selected columns <M> (M=1, 2, 3, . . . , and m) in the light-receiving unit 23; transfers and outputs the noise signals received from each of the unit pixels 230 at the time of pixel reset in each of the unit pixels 230 to the first horizontal transfer line 259 via the first sample hold units 242; and transfers and outputs the noise signals to the third horizontal transfer line 261 via the second sample hold units 243. Furthermore, the horizontal scanning unit 244 applies, based on the driving pulse (ϕH) supplied from the timing generating unit 25, the column selection pulse ϕH<M> in the selected column <M> in the light-receiving unit 23; transfers and outputs the imaging signals subjected to photoelectric conversion by each of the unit pixels 230 to the second horizontal transfer line 260 via the first sample hold units 242; and transfers and outputs the imaging signals to the fourth horizontal transfer line 262 via the second sample hold units 243. Furthermore, in the first embodiment, the vertical scanning unit 241 and the horizontal scanning unit 244 function as the reading unit 24.

A large number of the unit pixels 230 are arrayed in a two-dimensional matrix in the light-receiving unit 23 in the first chip 21. Each of the unit pixels 230 includes a photoelectric conversion element 231 (photodiode) and a photoelectric conversion element 232, a charge voltage converter 233, a transfer transistor 234 (first transferring unit) and a transfer transistor 235, a charge voltage converter reset unit 236 (transistor), a pixel source follower transistor 237, and a pixel output switch 238 (signal output unit). Furthermore, in this application, one or a plurality of photoelectric conversion elements and transfer transistors for transferring the signal charge from each of the photoelectric conversion elements to the charge voltage converters 233 are referred to as a unit cell. Namely, a set of one or a plurality of photoelectric conversion elements and transfer transistors is included in the unit cell and a single unit cell is included in each of the unit pixels 230. Furthermore, in the first embodiment, two pixels (the photoelectric conversion element 231 and the photoelectric conversion element 232) are provided in each of the unit pixels 230 and are allowed to share the single vertical transfer line 239 (first transfer line); however, the embodiment is not limited to this. For example, four or eight pixels may also be allowed to share the single vertical transfer line 239.

The photoelectric conversion element 231 and the photoelectric conversion element 232 perform photoelectric conversion on incident light to the signal charge level that is in accordance with the light level of the incident light and accumulate the signal charge. Regarding the photoelectric conversion element 231 and the photoelectric conversion element 232, each of the cathode sides thereof is connected to one end of the transfer transistor 234 and the transfer transistor 235 and each of the anode side is connected to the ground GND. The charge voltage converter 233 is formed by floating diffusion capacitor (FD) and converts the charge accumulated by the photoelectric conversion element 231 and the photoelectric conversion element 232 to a voltage.

The transfer transistor 234 and the transfer transistor 235 transfer a charge from the photoelectric conversion element 231 and the photoelectric conversion element 232, respectively, to the charge voltage converter 233. A signal line through which the driving pulses ϕT1<M> and ϕT2<M> are supplied is connected to each of the gates of the transfer transistor 234 and the transfer transistor 235 and the charge voltage converter 233 is connected to the other end thereof. If the driving pulses ϕT1 and ϕT2 are supplied from the vertical scanning unit 241 via the signal lines, the transfer transistor 234 and the transfer transistor 235 enter the on state and transfer the signal charge from the photoelectric conversion element 231 and the photoelectric conversion element 232, respectively, to the charge voltage converter 233.

The charge voltage converter reset unit 236 resets the charge voltage converter 233 to a predetermined electric potential. One end of the charge voltage converter reset unit 236 is connected to the power supply voltage VDD, the other end thereof is connected to the charge voltage converter 233, a signal line through which the driving pulse ϕR<M> is supplied is connected to the gate. If the driving pulse ϕR<M> is supplied from the vertical scanning unit 241 via the signal line, the charge voltage converter reset unit 236 enters the on state, emits the signal charge accumulated in the charge voltage converter 233, and resets the charge voltage converter 233 to the predetermined electric potential.

One end of the pixel source follower transistor 237 is connected to the power supply voltage VDD, the other end thereof is connected to one end of the pixel output switch 238, and a signal (image signal or signal at the time of reset) subjected to charge voltage conversion by the charge voltage converter 233 is input to the gate.

The pixel output switch 238 outputs the signal subjected to charge voltage conversion by the charge voltage converter 233 to the vertical transfer line 239. The other end of the pixel output switch 238 is connected to the vertical transfer line 239 and a signal line through which the row selection pulse ϕX<M> is supplied is connected to the gate. If the row selection pulse ϕX<M> is supplied to the gate of the pixel output switch 238 from the vertical scanning unit 241 via the signal line, the pixel output switch 238 enters the on state and transfers an image signal or the signal (noise signal) at the time of reset to the vertical transfer line 239.

The horizontal reset unit 245 resets, based on a driving pulse ϕhclr that is input from the timing generating unit 25, each of the first horizontal transfer line 259, the second horizontal transfer line 260, the third horizontal transfer line 261, and the fourth horizontal transfer line 262. The horizontal reset unit 245 includes a first horizontal reset transistor 271, a second horizontal reset transistor 272, a third horizontal reset transistor 273, and a fourth horizontal reset transistor 274.

One end of the first horizontal reset transistor 271 is connected to the reference voltage VREF, the other end thereof is connected to the first horizontal transfer line 259, a signal line to which the driving pulse ϕhclr is input from the timing generating unit 25 is connected to the gate. If the driving pulse ϕhclr is input from the timing generating unit 25 to the gate of the first horizontal reset transistor 271, the first horizontal reset transistor 271 enters the on state and resets the first horizontal transfer line 259.

One end of the second horizontal reset transistor 272 is connected to the reference voltage VREF, the other end thereof is connected to the second horizontal transfer line 260, and a signal line to which the driving pulse ϕhclr is input from the timing generating unit 25 is connected to the gate. If the driving pulse ϕhclr is input from the timing generating unit 25 to the gate of the second horizontal reset transistor 272, the second horizontal reset transistor 272 enters the on state and resets the second horizontal transfer line 260.

One end of the third horizontal reset transistor 273 is connected to the reference voltage VREF, the other end thereof is connected to the third horizontal transfer line 261, and the signal line to which the driving pulse ϕhclr is input from the timing generating unit 25 is connected to the gate. If the driving pulse ϕhclr is input from the timing generating unit 25 to the gate of the third horizontal reset transistor 273, the third horizontal reset transistor 273 enters the on state and resets the third horizontal transfer line 261.

One end of the fourth horizontal reset transistor 274 is connected to the reference voltage VREF, the other end thereof is connected to the fourth horizontal transfer line 262, and the signal line to which the driving pulse ϕhclr is input from the timing generating unit 25 is connected to the gate. When the driving pulse ϕhclr is input from the timing generating unit 25 to the gate of the fourth horizontal reset transistor 274, the fourth horizontal reset transistor 274 enters the on state and resets the fourth horizontal transfer line 262.

By obtaining a difference between the noise signal and the imaging signal transferred from each of the first horizontal transfer line 259 to the fourth horizontal transfer line 262, the output unit 31 externally outputs the imaging signal from which noise has been removed. The output unit 31 includes a first output amplification unit 311 and a second output amplification unit 312.

The first output amplification unit 311 is formed by using a differential amplifier and externally outputs, by obtaining a difference between the imaging signals in the odd numbered columns transferred from the first horizontal transfer line 259 and the noise signals in the odd numbered columns transferred from the second horizontal transfer line 260, the imaging signals that are in the odd numbered columns and from which noise has been removed (Vout1).

The second output amplification unit 312 is formed by using a differential amplifier and externally outputs, by obtaining a difference between the imaging signals in the even numbered columns transferred from the third horizontal transfer line 261 and the noise signals in the even numbered columns transferred from the fourth horizontal transfer line 262, the imaging signals that are in the even numbered columns and from which noise has been removed (Vout2).

Operation of the Imaging Unit

Figure 4:
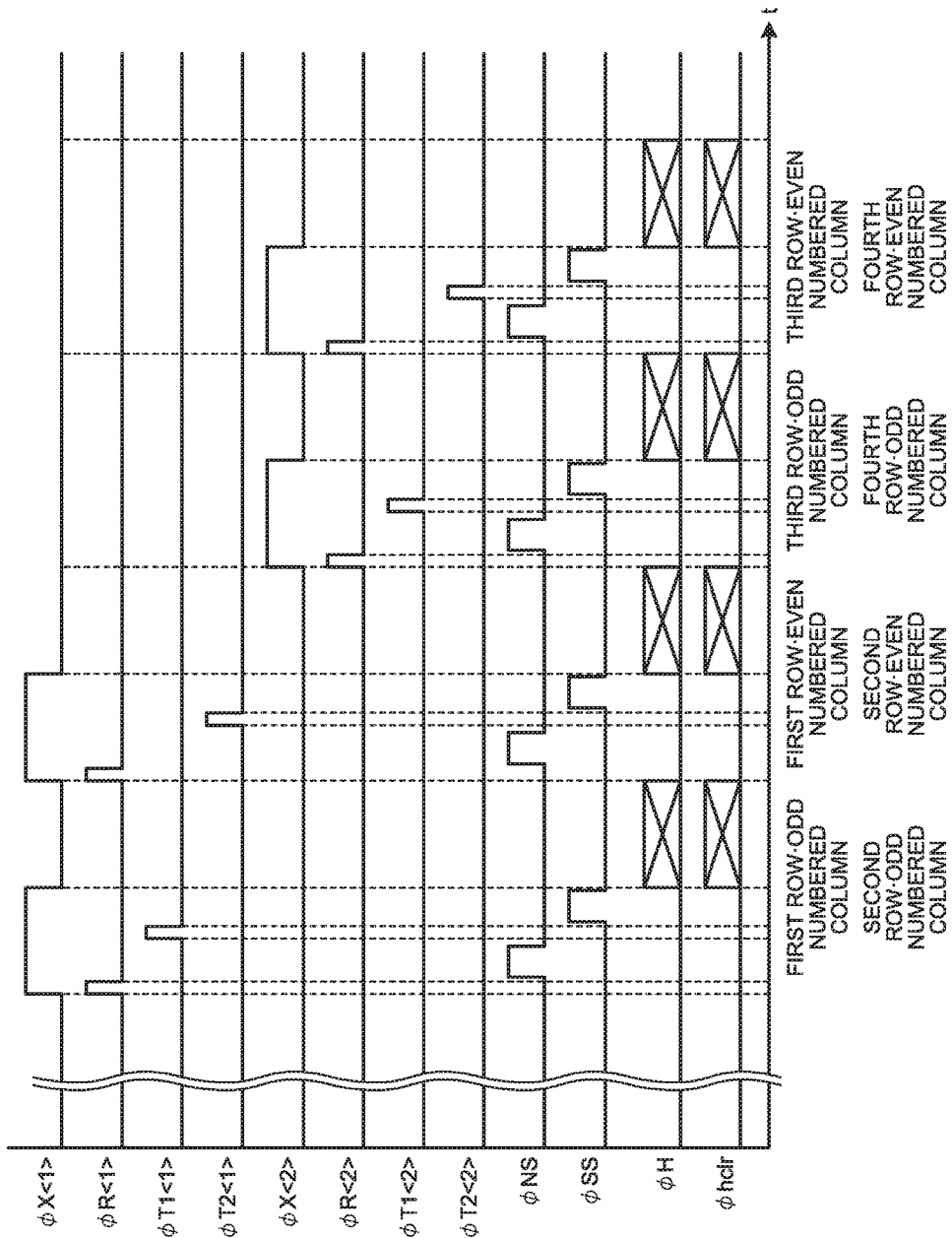
FIG. 4 is a timing chart illustrating a driving timing of an imaging unit according to the first embodiment.

In the following, a driving timing of the imaging unit 20 will be described. FIG. 4 is a timing chart illustrating a driving timing of the imaging unit 20 according to the first embodiment. FIG. 4 illustrates the timing of, in the order from the top, a row selection pulse ϕX<1>, a driving pulse ϕR<1>, a driving pulse ϕT1<1>, a driving pulse ϕT2<1>, a row selection pulse ϕX<2>, a driving pulse ϕR<2>, a driving pulse ϕT1<2>, a driving pulse ϕT2<2>, a driving pulse ϕNS, a driving pulse ϕSS, a column selection pulse ϕH, and a driving pulse ϕhclr.

As illustrated in FIG. 4, first, the timing generating unit 25 sets the row selection pulse ϕX<1> and the driving pulse ϕR<1> to the on state (High). Consequently, each of the charge voltage converter reset units 236 in the first row and the second row enters the on state, emits the signal charge accumulated in each of the charge voltage converters 233 in the first row and the second row, and resets each of the charge voltage converters 233 in the first row and the second row to a predetermined electric potential.

Subsequently, the timing generating unit 25 sets the driving pulse ϕR<1> to the off state (Low), sets the driving pulse ϕNS to the on state (High), allows the first sampling units 252 to sample the noise signals input from the charge voltage converters 233 in the first row via the vertical transfer lines 239 (239a), and allow the first sampling units 252a to sample the noise signals input from the charge voltage converters 233 in the second row via the vertical transfer lines 239 (239b).

Then, the timing generating unit 25 sets the driving pulse ϕNS to the off state (Low). Consequently, the first sampling units 252 complete the sampling of the noise signals in the first row. Furthermore, the first sampling units 252a complete the sampling of the noise signals in the second row.

Subsequently, the timing generating unit 25 sets the driving pulse ϕT1<1> to the on state (High) and sets the driving pulse ϕSS to the on state (High). In this case, each of the transfer transistors 234 in the first row and the second row enters the on state due to the driving pulse ϕT1<1> being input to the gate from the timing generating unit 25 and then transfers the signal charge from each of the photoelectric conversion elements 231 to the charge voltage converters 233 in the odd numbered columns in the first row and the second row. At this time, each of the pixel output switches 238 in the first row outputs the imaging signals subjected to charge voltage conversion by the charge voltage converters 233 from the pixel source follower transistors 237 to the vertical transfer lines 239 (239a), whereas each of the pixel output switches 238 in the second row outputs the imaging signals subjected to charge voltage conversion by the charge voltage converters 233 from the pixel source follower transistors 237 to the vertical transfer lines 239 (239b). Furthermore, the second sampling units 255 sample the imaging signals in the odd numbered columns in the first row output from the vertical transfer lines 239 (239a), whereas the second sampling units 255a sample the imaging signals in the odd numbered columns in the second row output from the vertical transfer lines 239 (239b).

Then, after having set the driving pulse φSS to the off state (Low), the timing generating unit 25 sets the row selection pulse φX<1> to the off state (Low) and sequentially repeats, for each column, the on/off operation of the column selection pulse φH<M> and the driving pulse φhclr. In this case, each of the second sampling units 255 transfers the sampled imaging signals in the odd numbered columns in the first row to the first horizontal transfer line 259 and outputs the transferred imaging signals to the first output amplification unit 311, whereas each of the first sampling units 252 transfers the sampled noise signals in the odd numbered columns in the first row to the second horizontal transfer line 260 and outputs the transferred noise signals to the first output amplification unit 311. The first output amplification unit 311 outputs a difference between the imaging signals and the noise signals in the odd numbered columns in the first row, whereby the imaging signals, from which noise has been removed, in the odd numbered columns in the first row are output (Vout1).

Furthermore, each of the second sampling units 255a transfers the sampled imaging signals in the odd numbered columns in the second row to the third horizontal transfer line 261 and outputs the transferred imaging signals to the second output amplification unit 312, whereas each of the first sampling units 252a transfers the sampled noise signals in the odd numbered columns in the second row to the fourth horizontal transfer line 262 and outputs the transferred noise signals to the second output amplification unit 312. The second output amplification unit 312 outputs a difference between the imaging signals and the noise signals in the odd numbered columns in the second row, whereby the imaging signals, from which noise has been removed, in the odd numbered columns in the second row are output (Vout2).

Then, the timing generating unit 25 sets the row selection pulse φX<1> and the driving pulse φR<1> to the on state (High). Consequently, each of the charge voltage converter reset units 236 in the first row and the second row enters the on state, emits the signal charge accumulated in each of the charge voltage converters 233 in the first row and the second row, and resets each of the charge voltage converters 233 to a predetermined electric potential.

Subsequently, the timing generating unit 25 sets the driving pulse φR<1> to the off state (Low), sets the driving pulse φNS to the on state (High), allows the first sampling units 252 to sample the noise signals input from the charge voltage converters 233 in the first row via the vertical transfer lines 239 (239a), and allow the first sampling units 252a to sample the noise signals input from the charge voltage converters 233 in the second row via the vertical transfer lines 239 (239b).

Then, the timing generating unit 25 sets the driving pulse φNS to the off state (Low). Consequently, the first sampling units 252 complete the sampling of the noise signals in the first row. Furthermore, the first sampling units 252a complete the sampling of the noise signals in the second row.

Subsequently, the timing generating unit 25 sets the driving pulse φT2<1> to the on state (High) and sets the driving pulse φSS to the on state (High). In this case, each of the transfer transistors 235 in the first row and the second row enters the on state due to the driving pulse φT2<1> being input to the gate from the timing generating unit 25 and then transfers the signal charge from each of the photoelectric conversion elements 232 in the even numbered columns in the first row and the second row to the charge voltage converters 233. At this time, the pixel output switches 238 in the first row output the imaging signals that have been subjected to charge voltage conversion by the charge voltage converters 233 from the pixel source follower transistors 237 in the first row to the vertical transfer lines 239 (239a), whereas the pixel output switches 238 in the second row outputs the imaging signals that have been subjected to charge voltage conversion by the charge voltage converters 233 from the pixel source follower transistors 237 in the second row to the vertical transfer lines 239 (239b). Furthermore, each of the second sampling units 255 samples the imaging signals output from the vertical transfer lines 239 (239a), whereas each of the second sampling unit 255a samples the imaging signals output from the vertical transfer lines 239 (239b).

Then, after having set the driving pulse φSS to the off state (Low), the timing generating unit 25 sets the row selection pulse φX<1> to the off state (Low) and sequentially repeats, for each column, the on/off operation of the column selection pulse φH<M> and the driving pulse φhclr. In this case, each of the second sampling units 255 transfers the sampled imaging signals in the even numbered columns in the first row to the first horizontal transfer line 259 and outputs the transferred imaging signals to the first output amplification unit 311, whereas each of the first sampling units 252 transfers the sampled noise signals in the even numbered columns in the first row to the second horizontal transfer line 260 and outputs the transferred noise signals to the first output amplification unit 311. The first output amplification unit 311 outputs a difference between the imaging signals and the noise signals in the even numbered columns in the first row, whereby the imaging signals, from which noise has been removed, in the even numbered columns in the first row are output (Vout1).

Furthermore, each of the second sampling units 255a transfers the sampled imaging signals in the even numbered columns in the second row to the third horizontal transfer line 261 and outputs the transferred imaging signals to the second output amplification unit 312, whereas each of the first sampling units 252a transfers the sampled noise signals in the even numbered columns in the second row to the fourth horizontal transfer line 262 and outputs the transferred noise signals to the second output amplification unit 312. The second output amplification unit 312 outputs the difference between the imaging signals and the noise signals in the even numbered columns in the second row, whereby the imaging signals, from which noise has been removed, in the even numbered columns in the second row are output (Vout2).

Subsequently, the timing generating unit 25 sets the row selection pulse φX<2> and the driving pulse φR<2> to the on state (High). Consequently, each of the charge voltage converter reset units 236 in the third row and the fourth row enters the on state, emits the signal charge accumulated in each of the charge voltage converters 233 in the third row and the fourth row, and resets each of the charge voltage converters 233 in the third row and the fourth row to a predetermined electric potential.

Subsequently, the timing generating unit 25 sets the driving pulse φR<2> to the off state (Low), sets the driving pulse φNS to the on state (High), allows the first sampling units 252 to sample the noise signals input from the charge voltage converters 233 in the third row via the vertical transfer lines 239 (239a), and allows the first sampling units 252a to sample the noise signals input from the charge voltage converters 233 in the fourth row via the vertical transfer lines 239 (239b).

Then, the timing generating unit 25 sets the driving pulse φNS to the off state (Low). Consequently, the first sampling units 252 complete the sampling of the noise signals in the third row. Furthermore, the first sampling units 252a complete the sampling of the noise signals in the fourth row.

Subsequently, the timing generating unit 25 sets the driving pulse φT1<2> to the on state (High) and sets the driving pulse φSS to the on state (High). In this case, each of the transfer transistors 234 in the third row and the fourth row enters the on state due to the driving pulse φT1<2> being input to the gate from the timing generating unit 25 and then transfers the signal charge from the photoelectric conversion elements 231 in each of the odd numbered columns in the third row and the fourth row to the charge voltage converters 233. At this time, the pixel output switches 238 in the third row output the imaging signals subjected to charge voltage conversion by the charge voltage converters 233 from the pixel source follower transistors 237 to the vertical transfer lines 239 (239a), whereas the pixel output switches 238 in the fourth row outputs the imaging signals subjected to charge voltage conversion by the charge voltage converters 233 from the pixel source follower transistors 237 to the vertical transfer lines 239 (239b). Furthermore, the second sampling units 255 sample the imaging signals output from the vertical transfer lines 239 (239a), whereas the second sampling units 255a sample the imaging signals output from the vertical transfer lines 239 (239b).

Then, after having set the driving pulse φSS to the off state (Low), the timing generating unit 25 sets the row selection pulse φX<2> to the off state (Low) and sequentially repeats, for each column, the on/off operation of the column selection pulse φH<M> and the driving pulse φhclr. In this case, each of the second sampling units 255 transfers the sampled imaging signals in the odd numbered columns in the third row to the first horizontal transfer line 259 and outputs the transferred imaging signals to the first output amplification unit 311, whereas each of the first sampling units 252 transfers the sampled noise signals in the third row to the second horizontal transfer line 260 and outputs the transferred noise signals to the first output amplification unit 311. The first output amplification unit 311 outputs a difference between the imaging signals and the noise signals in the odd numbered columns in the third row, whereby the imaging signals, from which noise has been removed, in the odd numbered columns in the third row are output (Vout1).

Furthermore, each of the second sampling units 255a transfers the sampled imaging signals in the odd numbered columns in the fourth row to the third horizontal transfer line 261 and outputs the transferred imaging signals to the second output amplification unit 312, whereas each of the first sampling units 252a transfers the sampled noise signals in the fourth row to the fourth horizontal transfer line 262 and outputs the transferred noise signals to the second output amplification unit 312. The second output amplification unit 312 outputs the difference between the imaging signals and the noise signals in the odd numbered columns in the fourth row, whereby the imaging signals, from which noise has been removed, in the odd numbered columns in the fourth row are output (Vout2).

Then, the timing generating unit 25 sets the row selection pulse φX<2> and the driving pulse φR<2> to the on state (High). Consequently, each of the charge voltage converter reset units 236 in the third row and the fourth row enters the on state, emits the signal charge accumulated in each of the charge voltage converters 233 in the third row and the fourth row, and resets the charge voltage converters 233 to the predetermined electric potential.

Subsequently, the timing generating unit 25 sets the driving pulse φR<2> to the off state (Low), sets the driving pulse φNS to the on state (High), allows the first sampling units 252 to sample the noise signals input from the charge voltage converters 233 in the third row via the vertical transfer lines 239 (239a), and allows the first sampling units 252a to sample the noise signals input from the charge voltage converters 233 in the fourth row via the vertical transfer lines 239 (239b).

Then, the timing generating unit 25 sets the driving pulse φNS to the off state (Low). Consequently, the first sampling units 252 complete the sampling of the noise signals in the third row. Furthermore, the first sampling units 252a complete the sampling of the noise signals in the fourth row.

Subsequently, the timing generating unit 25 sets the driving pulse φT2<2> to the on state (High) and sets the driving pulse φSS to the on state (High). In this case, each of the transfer transistors 235 in the third row and the fourth row enters the on state due to the driving pulse φT2<2> being input to the gate from the timing generating unit 25 and then transfers the signal charge from the photoelectric conversion elements 232 in each of the even numbered columns in the third row and the fourth row to the charge voltage converters 233. At this time, the pixel output switches 238 in the third row output the imaging signals subjected to charge voltage conversion by the charge voltage converters 233 from the pixel source follower transistors 237 in the third row to the vertical transfer lines 239 (239a), whereas the pixel output switches 238 in the fourth row output the imaging signals subjected to charge voltage conversion by the charge voltage converters 233 from the pixel source follower transistors 237 in the fourth row to the vertical transfer lines 239 (239b). Furthermore, the second sampling units 255 sample the imaging signals output from the vertical transfer lines 239 (239a), whereas the second sampling units 255a sample the imaging signals output from the vertical transfer lines 239 (239b).

Then, after having set the driving pulse φSS to the off state (Low), the timing generating unit 25 sets the row selection pulse φX<2> to the off state (Low) and sequentially repeats, for each column, the on/off operation of the column selection pulse φH<M> and the driving pulse φhclr. In this case, each of the second sampling units 255 transfers the sampled imaging signals in the even numbered columns in the third row to the first horizontal transfer line 259 and outputs the transferred imaging signals to the first output amplification unit 311, whereas each of the first sampling units 252 transfers the sampled noise signals in the even numbered columns in the third row to the second horizontal transfer line 260 and outputs the transferred noise signals to the first output amplification unit 311. The first output amplification unit 311 outputs a difference between the imaging signals and the noise signals in the even numbered columns in the third row, whereby the imaging signals, from which noise has been removed, in the even numbered columns in the third row are output (Vout1).

Furthermore, each of the second sampling units 255a transfers the sampled imaging signals in the even numbered columns in the fourth row to the third horizontal transfer line 261 and outputs the transferred imaging signals to the second output amplification unit 312, whereas each of the first sampling units 252a transfers the sampled noise signals in the even numbered columns in the fourth row to the fourth horizontal transfer line 262 and outputs the transferred noise signals to the second output amplification unit 312. The second output amplification unit 312 outputs the difference between the imaging signals and the noise signals in the even numbered columns in the fourth row, whereby the imaging signals, from which noise has been removed, in the even numbered columns in the fourth row are output (Vout2).

In this way, by controlling each of the vertical scanning unit 241, the first sample hold units 242, the second sample hold units 243, the horizontal scanning unit 244, and the horizontal reset unit 245, the timing generating unit 25 simultaneously (in parallel) and alternately, between the odd numbered columns and the even numbered columns, outputs the imaging signals from each of the plurality of the unit pixels 230 that are located in two different rows.

According to the first embodiment described above, the timing generating unit 25 simultaneously drives the pixels in the plurality of rows adjacent in the row direction (vertical direction) and simultaneously (in parallel) outputs, to the first output amplification unit 311 and the second output amplification unit 312, the plurality of imaging signals output from the pixels in these plurality of rows; therefore, the time needed to read the imaging signal from each of the unit pixels 230 may be reduced to half, and it is thus possible to implement a reduction in size and readout at high speed.

Furthermore, according to the first embodiment, by controlling each of the vertical scanning unit 241, the first sample hold units 242, the second sample hold units 243, the horizontal scanning unit 244, and the horizontal reset unit 245, the timing generating unit 25 simultaneously (in parallel) and alternately outputs the imaging signals in the odd numbered columns and the even numbered columns from each of the plurality of the unit pixels 230 that are located in two different rows, which makes it possible to output the imaging signals at a low speed and thus implementing low electrical power consumption and saving transmission bands. Furthermore, because the imaging unit 20 may be driven with low electrical power consumption, it is possible to prevent the distal end 101 of the endoscope 2 from becoming high temperature.

Furthermore, in the first embodiment, the timing generating unit 25, the first sample hold units 242, the second sample hold units 243, the horizontal reset unit 245, and the output unit 31 are provided on the first chip 21; however, these units may also be provided on the second chip 22. Consequently, the size of the first chip 21 may be further reduced and the size of the imaging unit 20 (image sensor) may also be reduced.

Second Embodiment

In the following, a second embodiment according to the present disclosure will be described. In an endoscope system according to the second embodiment, the configuration of the first chip is different. Specifically, regarding the first chip 21 according to the first embodiment described above, the sample hold unit is provided in each of the vertical transfer lines 239; however, in the second embodiment, a clamp hold unit is provided in each of the vertical transfer lines 239. Furthermore, in the second embodiment, instead of the horizontal reset unit, each of amplifiers and sample hold units is provided in each of the horizontal transfer lines. In a description below, the configuration of the first chip according to the second embodiment will be described and then the operation of the imaging unit according to the second embodiment will be described. Furthermore, components that are identical to those in the endoscope system 1 according to the first embodiment are assigned the same reference numerals and descriptions thereof will be omitted.

Configuration of the First Chip

Figure 5:
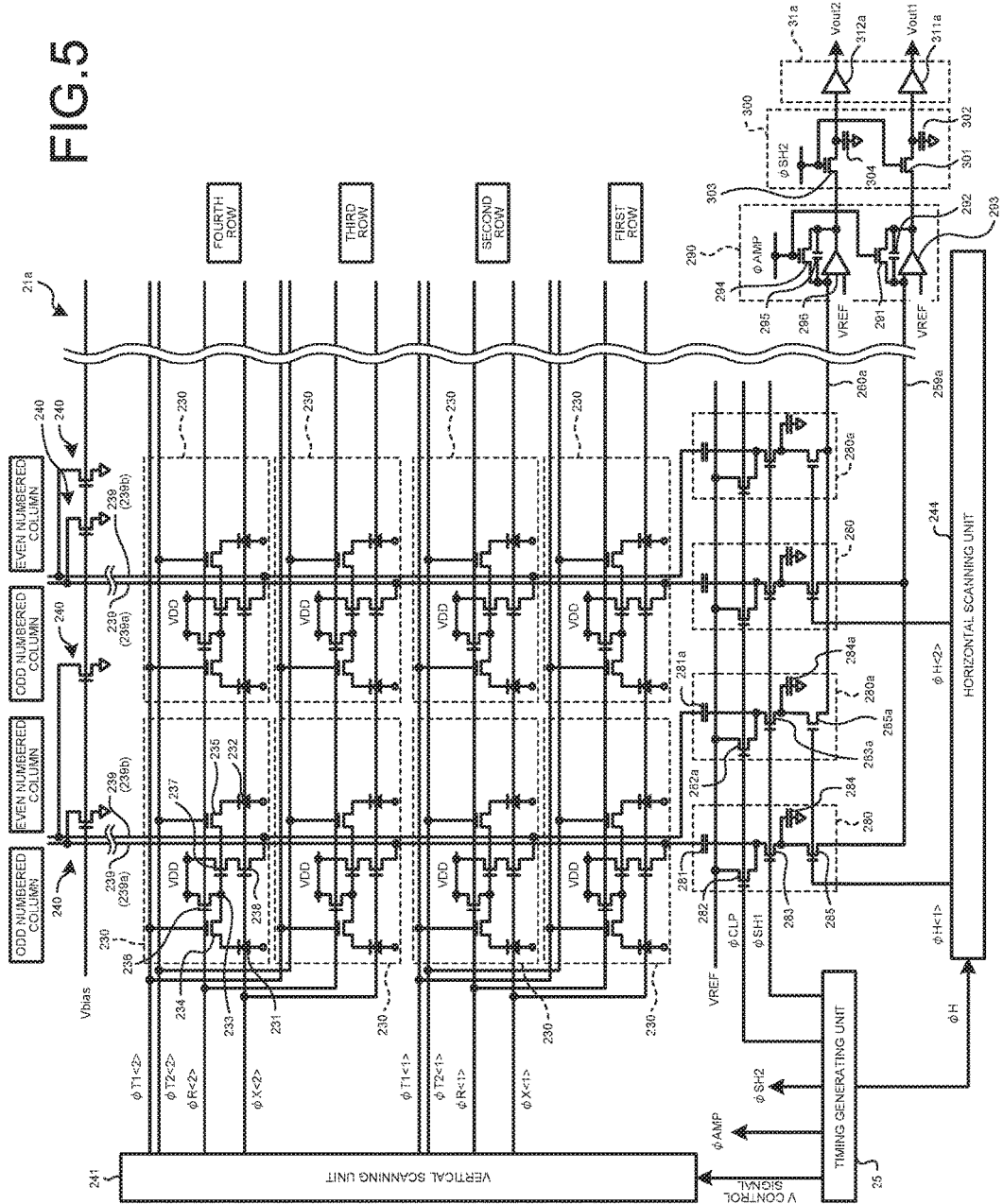
FIG. 5 is a circuit diagram illustrating the configuration of a first chip according to a second embodiment.

FIG. 5 is a circuit diagram illustrating the configuration of a first chip according to a second embodiment. Instead of the first sample hold units 242, the second sample hold units 243, and the horizontal reset unit 245 in the first chip 21 according to the first embodiment described above, a first chip 21a illustrated in FIG. 5 includes first clamp hold units 280, second clamp hold units 280a, an amplifier 290, and a sample hold unit 300.

The first clamp hold units 280 are provided in the vertical transfer line 239 (239a) in the odd numbered columns. After having clamped the noise signal at the time of pixel reset in each of the unit pixels 230, each of the first clamp hold units 280 removes noise by reading the imaging signal that has been subjected to photoelectric conversion by each of the unit pixels 230 and then outputs the imaging signal from which noise has been removed to the amplifier 290. Each of the first clamp hold units 280 includes a third sampling unit 281, a clamp switch 282, a third sampling switch 283, a fourth sampling unit 284, and a third output switch 285.

One end of the third sampling unit 281 is connected to the vertical transfer line 239 (239a) and the other end thereof is connected to the third sampling switch 283. When the row selection pulse φX<M> and the driving pulse φR<M> are applied to the unit pixels 230, by changing the driving pulse φCLP from the on state to the off state, the third sampling unit 281 clamps the noise signals received from the unit pixels 230 and then removes, by applying the row selection pulse φX<M> and the driving pulse φT1<M> or the driving pulse φT2<M> to the unit pixels 230, the noise component of the imaging signals received from the unit pixels 230.

The signal line through which the reference voltage VREF is supplied is connected to one end of the clamp switch 282, the other end thereof is connected between the third sampling unit 281 and the third sampling switch 283, and the signal line through which the driving pulse φCLP is supplied from the timing generating unit 25 is connected to the gate.

One end of the third sampling switch 283 is connected to the third sampling unit 281, the other end thereof is connected to one end of the third output switch 285, and the signal line through which the driving pulse φSH1 is supplied from the timing generating unit 25 is connected to the gate.

One end of the fourth sampling unit 284 is connected to the ground GND and the other end thereof is connected between the third sampling switch 283 and the third output switch 285. When the clamp switch 282 enters the on state, the fourth sampling unit 284 is reset to a predetermined electric potential by the reference voltage VREF.

One end of the third output switch 285 is connected to the third sampling switch 283, the other end thereof is connected to a first horizontal transfer line 259a, and the signal line through which the column selection pulse φH<M> is supplied from the horizontal scanning unit 244 is connected to the gate. When the column selection pulse φH<M> is applied to the gate, the third output switch 285 transfers, to the first horizontal transfer line 259a, the imaging signals that are present in the odd numbered columns, that are sampled by the fourth sampling unit 284, and from which noise has been removed.

The second clamp hold unit 280a is provided in the vertical transfer line 239 (239b) in the even numbered columns. After having clamped the noise signal at the time of pixel reset performed in each of the unit pixels 230, each of the second clamp hold units 280a removes noise by reading the imaging signal that has been subjected to photoelectric conversion by each of the unit pixels 230 and then outputs the imaging signal from which noise has been removed to the amplifier 290. The second clamp hold unit 280a includes a third sampling unit 281a, a clamp switch 282a, a third sampling switch 283a, a fourth sampling unit 284a, and a third output switch 285a.

One end of the third sampling unit 281a is connected to the vertical transfer line 239 (239b) and the other end thereof is connected to the third sampling switch 283a. When the row selection pulse φX<M> and the driving pulse φR<M> are applied to the unit pixels 230, by changing the state of the driving pulse φCLP from the on state to the off state, the third sampling unit 281a clamps the noise signals received from the unit pixels 230 and then removes, by applying the row selection pulse φX<M> and the driving pulse φT1<M> or the driving pulse φT2<M> to the unit pixels 230, the noise component of the imaging signals received from the unit pixels 230.

The signal line through which the reference voltage VREF is supplied is connected to one end of the clamp switch 282a, the other end thereof is connected between the third sampling unit 281a and the third sampling switch 283a, and the signal line through which the driving pulse φCLP is supplied from the timing generating unit 25 is connected to the gate.

One end of the third sampling switch 283a is connected to the third sampling unit 281a, the other end thereof is connected to one end of the third output switch 285a, and the signal line through which the driving pulse φSH1 is supplied from the timing generating unit 25 is connected to the gate.

One end of the fourth sampling unit 284a is connected to the ground GND and the other end thereof is connected between the third sampling switch 283a and the third output switch 285a. When the clamp switch 282a enters the on state, the fourth sampling unit 284a is reset to a predetermined electric potential by the reference voltage VREF.

One end of the third output switch 285a is connected to the third sampling switch 283a, the other end thereof is connected to a second horizontal transfer line 260a, and the signal line through which the column selection pulse φH<M> is supplied from the horizontal scanning unit 244 is connected to the gate. When the column selection pulse φH<M> is applied to the gate, the third output switch 285a transfers, to the second horizontal transfer line 260a, the imaging signals that are present in the even numbered columns, that are sampled by the fourth sampling unit 284a, and from which noise has been removed.

The amplifier 290 holds the imaging signals from which noise has been removed and that are input from the first horizontal transfer line 259a or the second horizontal transfer line 260a and then outputs the imaging signals from which noise has been removed to the sample hold unit 300, while sequentially changing the on/off operation based on the driving pulse φAMP that is input from the timing generating unit 25. The amplifier 290 includes a first amplifier switch 291, a first amp capacitor 292, a first operational amplifier 293, a second amplifier switch 294, a second amp capacitor 295, and a second operational amplifier 296.

One end of the first amplifier switch 291 is connected to the first horizontal transfer line 259a, the other end thereof is connected to the sample hold unit 300, and the signal line through which the driving pulse φAMP is supplied from the timing generating unit 25 is connected to the gate.

One end of the first amp capacitor 292 is connected between the first horizontal transfer line 259a and the first amplifier switch 291 and the other end thereof is connected between the first amplifier switch 291 and the sample hold unit 300.

The first horizontal transfer line 259a is connected to the plus terminal section of the input side of the first operational amplifier 293, the signal line through which the reference voltage VREF is supplied is connected to the minus terminal section on the input side, and the sample hold unit 300 is connected to the output side of the first operational amplifier 293. Furthermore, an output of the first operational amplifier 293 is input, via the first amp capacitor 292, to the plus terminal section of the input side of the first operational amplifier 293.

One end of the second amplifier switch 294 is connected to the second horizontal transfer line 260a, the other end thereof is connected to the sample hold unit 300, and the signal line through which the driving pulse φAMP is supplied from the timing generating unit 25 is connected to the gate.

One end of the second amp capacitor 295 is connected between the second horizontal transfer line 260a and the second amplifier switch 294 and the other end thereof is connected between the second amplifier switch 294 and the sample hold unit 300.

the second horizontal transfer line 260a is connected to the plus terminal section of the input side of the second operational amplifier 296, the signal line through which the reference voltage VREF is supplied is connected to the minus terminal section on the input side, and the sample hold unit 300 is connected to the output side of the second operational amplifier 296. Furthermore, an output of the second operational amplifier 296 is input, via the second amp capacitor 295, to the plus terminal section of the input side of the second operational amplifier 296.

The amplifier 290 configured in this way multiplies imaging signals held in the fourth sampling unit 284 and the fourth sampling unit 284a by the gain that is determined by the ratio of the capacity values of the first amp capacitor 292 and the second amp capacitor 295, the capacity values of the fourth sampling unit 284 and the fourth sampling unit 284a, and the capacity values of the third sampling unit 281 and the third sampling unit 281a and then outputs the results to the sample hold unit 300.

The sample hold unit 300 holds the imaging signals input from the amplifier 290 and outputs the imaging signals to an output unit 31a based on the driving pulse φSH2 that is input from the timing generating unit 25.

The sample hold unit 300 includes a fourth sampling switch 301, a fifth sampling unit 302, a fifth sampling switch 303, and a sixth sampling unit 304.

One end of the fourth sampling switch 301 is connected to the first operational amplifier 293, the other end thereof is connected to a first output amplification unit 311a, and the signal line through which the driving pulse φSH2 is supplied from the timing generating unit 25 is connected to the gate.

One end of the fifth sampling unit 302 is connected to the ground GND and the other end thereof is connected between the fourth sampling switch 301 and the first output amplification unit 311a.

One end of the fifth sampling switch 303 is connected to the second operational amplifier 296, the other end thereof is connected to a second output amplification unit 312a, and the signal line through which the driving pulse φSH2 is supplied from the timing generating unit 25 is connected to the gate.

One end of the sixth sampling unit 304 is connected to the ground GND and the other end thereof is connected between the fifth sampling switch 303 and the second output amplification unit 312a.

The output unit 31a includes the first output amplification unit 311a, and the second output amplification unit 312a. The first output amplification unit 311a amplifies the imaging signals output from the fifth sampling unit 302 and externally outputs the amplified imaging signals (Vout1). The second output amplification unit 312a amplifies the imaging signals externally output from the sixth sampling unit 304 and outputs the amplified imaging signals (Vout2).

Operation of the Imaging Unit

Figure 6:
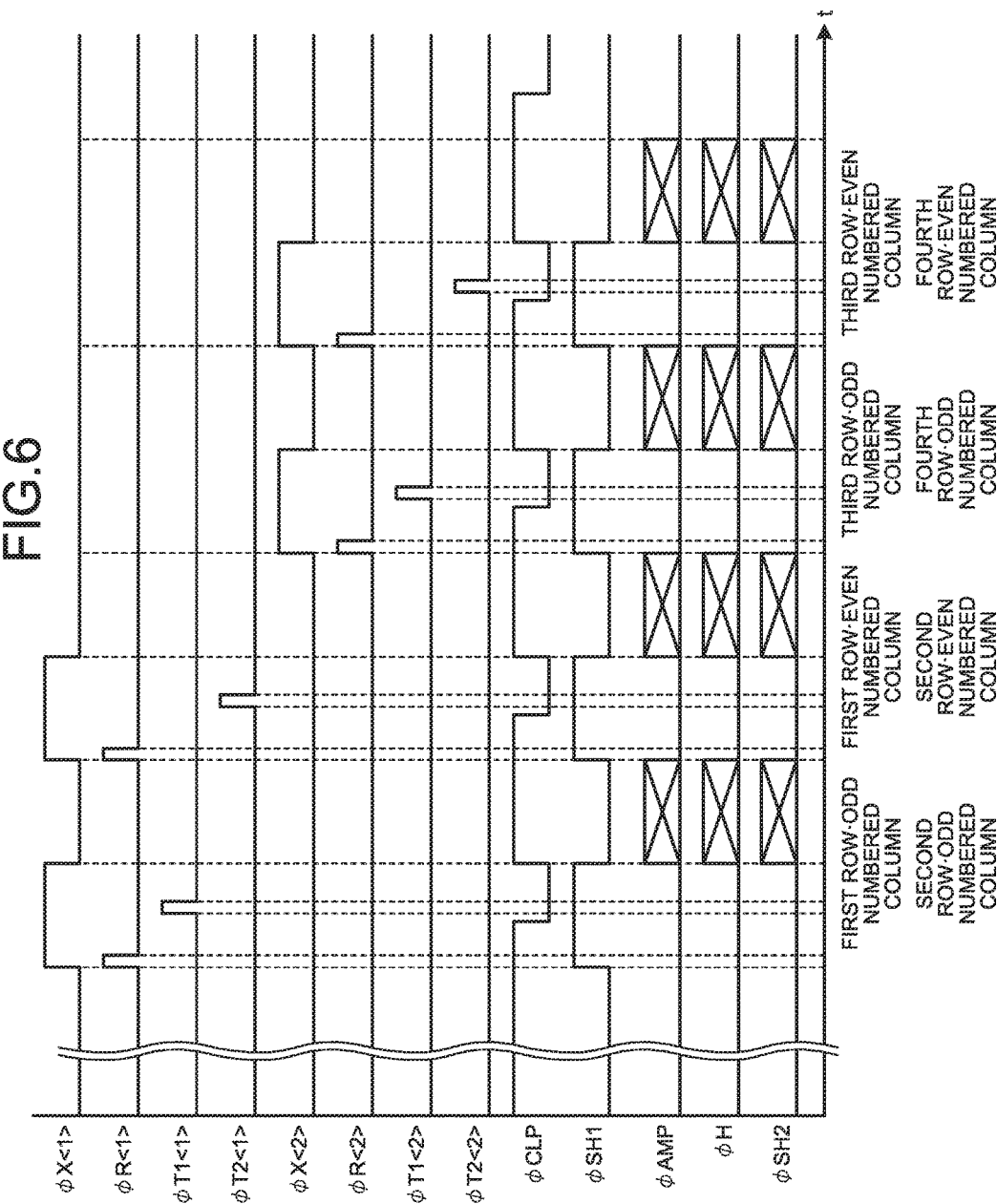
FIG. 6 is a timing chart illustrating a driving timing of an imaging unit according to the second embodiment.

In the following, a driving timing of the imaging unit 20 will be described. FIG. 6 is a timing chart illustrating a driving timing of the imaging unit 20 according to the second embodiment. FIG. 6 illustrates the timing of, in the order from the top, the row selection pulse φX<1>, the driving pulse φR<1>, the driving pulse φT1<1>, the driving pulse φT2<1>, the row selection pulse φX<2>, the driving pulse φR<2>, the driving pulse φT1<2>, the driving pulse φT2<2>, a driving pulse φCLP, a driving pulse φSH1, a driving pulse φAMP, a column selection pulse φH<m>, and a driving pulse φSH2.

As illustrated in FIG. 6, first, while maintaining the driving pulse φCLP in the on state, the timing generating unit 25 sets the row selection pulse φX<1>, the driving pulse φR<1>, and the driving pulse φSH1 to the on state (High). Consequently, each of the charge voltage converter reset units 236 in the first row and the second row enters the on state, emits the signal charge accumulated in each of the charge voltage converters 233 in the first row and the second row, and resets each of the charge voltage converters 233 in the first row and the second row to the predetermined electric potential.

subsequently, the timing generating unit 25 sets the driving pulse φR<1> to the off state (Low), allows the fourth sampling unit 284 to clamp the noise signals input from the charge voltage converters 233 in the first row via the vertical transfer lines 239 (239a) and the third sampling unit 281, and allows the fourth sampling units 284a to clamp the noise signals input from the charge voltage converters 233 in the second row via the vertical transfer lines 239 (239b) and the third sampling units 281a.

Then, the timing generating unit 25 sets the driving pulse φCLP to the off state (Low). Consequently, the fourth sampling units 284 complete the clamping of the noise signals in the first row. Furthermore, the fourth sampling units 284a complete the clamping of the noise signals in the second row.

Subsequently, the timing generating unit 25 sets the driving pulse φT1<1> to the on state (High). In this case, each of the transfer transistors 234 in the first row and the second row enters the on state due to the driving pulse φT1<1> being input to the gate from the timing generating unit 25 and transfers the signal charge from each of the photoelectric conversion elements 231 to the charge voltage converters 233 in the odd numbered columns in the first row and the second row. At this time, each of the pixel output switches 238 in the first row outputs the imaging signals subjected to charge voltage conversion by the charge voltage converters 233 from the pixel source follower transistors 237 to the vertical transfer lines 239 (239a), whereas each of the pixel output switches 238 in the second row outputs the imaging signals subjected to charge voltage conversion by the charge voltage converters 233 from the pixel source follower transistors 237 to the vertical transfer lines 239 (239b). Furthermore, the third sampling units 281 complete noise removal of the imaging signals in the odd numbered columns in the first row output from the vertical transfer lines 239 (239a), whereas the third sampling units 281a complete noise removal of the imaging signals in the odd numbered columns in the second row output from the vertical transfer lines 239 (239b).

Then, after having set the driving pulse φSH1 to the off state (Low), the timing generating unit 25 sets the row selection pulse φX<1> to the off state (Low), sets the driving pulse φCLP to the on state (High), and sequentially repeats, for each column, the on/off operation of the driving pulse φAMP, the column selection pulse φH<M>, and the driving pulse φSH2. In this case, each of the fourth sampling units 284 transfers, when the column selection pulse φH<M> is in the on state, the sampled imaging signals in the odd numbered columns in the first row to the first horizontal transfer line 259a and outputs the transferred imaging signals to the first operational amplifier 293. The fifth sampling unit 302 outputs the sampled imaging signals to the first output amplification unit 311a in accordance with the on/off operation of the fourth sampling switch 301. The first output amplification unit 311a externally outputs the imaging signals in the odd numbered columns in the first row input from the fifth sampling unit 302 (Vout1).

Furthermore, each of the fourth sampling units 284a transfers, when the column selection pulse φH<M> is in the on state, the sampled imaging signals in the odd numbered columns in the second row to the second horizontal transfer line 260a and outputs the transferred imaging signals to the second operational amplifier 296. The sixth sampling unit 304 outputs the sampled imaging signals to the second output amplification unit 312a in accordance with the on/off operation of the fifth sampling switch 303. The second output amplification unit 312a externally outputs the imaging signals in the odd numbered columns in the second row input from the sixth sampling unit 304 (Vout2).

Subsequently, the timing generating unit 25 sets the row selection pulse φX<1>, the driving pulse φR<1>, and the driving pulse φSH1 to the on state (High). Consequently, each of the charge voltage converter reset units 236 in the first row and the second row enters the on state, allows each of the charge voltage converters 233 in the first row and the second row to emit the signal charge, and resets each of the charge voltage converters 233 in the first row and the second row to a predetermined electric potential.

Then, the timing generating unit 25 sets the driving pulse φR<1> to the off state (Low), allows the fourth sampling units 284 to clamp the noise signals input from the charge voltage converters 233 in the first row via the vertical transfer lines 239 (239a) and the third sampling units 281, and allows the fourth sampling units 284a to clamp the noise signals input from the charge voltage converters 233 in the second row via the vertical transfer lines 239 (239b) and the third sampling units 281a.

Then, the timing generating unit 25 sets the driving pulse φCLP to the off state (Low). Consequently, the fourth sampling units 284 complete the clamping of the noise signals in the first row. Furthermore, the fourth sampling units 284a complete the clamping of the noise signals in the second row.

Subsequently, the timing generating unit 25 sets the driving pulse φT2<1> to the on state (High). In this case, each of the transfer transistors 235 in the first row and the second row enters the on state due to the driving pulse φT2<1> being input to the gate from the timing generating unit 25 and transfers the signal charge from the photoelectric conversion elements 232 to the charge voltage converters 233 in each of the even numbered columns in the first row and the second row. At this time, the pixel output switches 238 in the first row output the imaging signal subjected to charge voltage conversion by the charge voltage converter 233 from the pixel source follower transistors 237 to the vertical transfer lines 239 (239a), whereas the pixel output switches 238 in the second row output the imaging signals subjected to charge voltage conversion by the charge voltage converters 233 from the pixel source follower transistors 237 to the vertical transfer lines 239 (239b). Furthermore, the third sampling units 281 complete noise removal of the imaging signals in the even numbered columns in the first row output from the vertical transfer lines 239 (239a), whereas the third sampling units 281a complete noise removal of the imaging signals in the even numbered columns in the second row output from the vertical transfer lines 239 (239b).

Then, after having set the driving pulse φSH1 to the off state (Low), the timing generating unit 25 sets the row selection pulse φX<1> to the off state (Low), sets the driving pulse φCLP to the on state (High), and sequentially repeats, for each column, the on/off operation of the driving pulse φAMP, the column selection pulse φH<M>, and the driving pulse φSH2. In this case, each of the fourth sampling units 284 transfers, when the column selection pulse φH<M> is in the on state, the sampled imaging signals in the even numbered columns in the first row to the first horizontal transfer line 259a and outputs the transferred imaging signals to the first operational amplifier 293. The fifth sampling unit 302 outputs the sampled imaging signals to the first output amplification unit 311a in accordance with the on/off operation of the fourth sampling switch 301. The first output amplification unit 311a outputs the imaging signals in the even numbered columns in the first row input from the fifth sampling unit 302 to an external unit (Vout1).

Furthermore, each of the fourth sampling units 284a outputs, when the column selection pulse φH<M> is in the on state, the sampled imaging signals in the even numbered columns in the second row to the second horizontal transfer line 260a and outputs the transferred imaging signals to the second operational amplifier 296. The sixth sampling unit 304 outputs the sampled imaging signals to the second output amplification unit 312a in accordance with the on/off operation of the fifth sampling switch 303. The second output amplification unit 312a externally outputs the imaging signals in the even numbered columns in the second row input from the sixth sampling unit 304 (Vout2).

Subsequently, the timing generating unit 25 performs the on/off operation of the row selection pulse φX<2>, the driving pulse φR<2>, the driving pulse φT1<2>, the driving pulse φT2<2>, the driving pulse φCLP, the driving pulse φSH1, the driving pulse φAMP, the column selection pulse φH, and the driving pulse φSH2. Consequently, after having output the imaging signals in the odd numbered columns in the third row and the fourth row to an external unit, the timing generating unit 25 allows the imaging signals in the even numbered columns to output outside.

In this way, by controlling each of the vertical scanning unit 241, the first clamp hold units 280, the second clamp hold units 280a, the amplifier 290, and the sample hold unit 300, the timing generating unit 25 simultaneously and alternately outputs the imaging signals in the odd numbered columns and the even numbered columns from each of the plurality of the unit pixels 230 located in two different rows to an external unit.

According to the second embodiment described above, the timing generating unit 25 simultaneously drives the pixels in the plurality of rows adjacent in the row direction (vertical direction) and simultaneously (in parallel) outputs, to the first output amplification unit 311a and the second output amplification unit 312a, the plurality of imaging signals output from the pixels in these plurality of rows; therefore, the time needed to read the imaging signal from each of the unit pixels 230 may be reduced to half, and it is thus possible to implement a reduction in size and readout at high speed.

Third Embodiment

In the following, a third embodiment will be described. In an endoscope system according to the third embodiment, the configuration of the first chip is different from that described in the second embodiment. Specifically, in the first chip according to the third embodiment, the sample hold circuit is eliminated from a clamp hold circuit. In a description below, the configuration of the first chip according to the third embodiment will be described and then the operation of the imaging unit according to the third embodiment will be described. Furthermore, components that are identical to those in the endoscope system 1 according to the second embodiment are assigned the same reference numerals and descriptions thereof will be omitted.

Configuration of the First Chip

Figure 7:
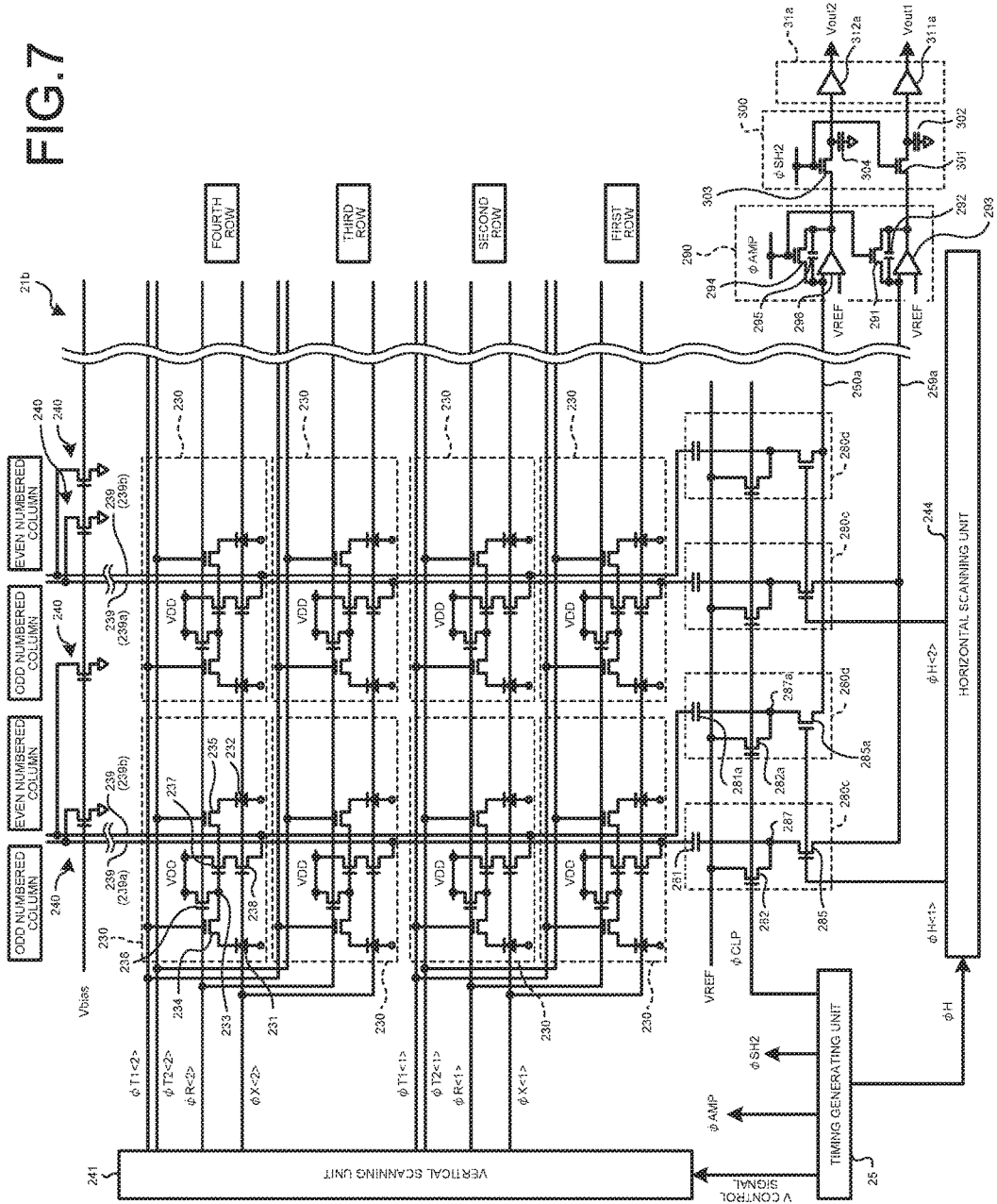
FIG. 7 is a circuit diagram illustrating the configuration of a first chip according to a third embodiment.

FIG. 7 is a circuit diagram illustrating the configuration of a first chip according to a third embodiment. Instead of the first clamp hold units 280 and the second clamp hold units 280a in the first chip 21 according to the second embodiment described above, a first chip 21b illustrated in FIG. 7 includes first clamp hold units 280c and second clamp hold units 280d.

The first clamp hold units 280c are provided in the vertical transfer lines 239 (239a) in the odd numbered columns. The first clamp hold units 280c sample the imaging signals subjected to photoelectric conversion in each of the unit pixels 230 and then output the sampled imaging signals to the amplifier 290. Each of the first clamp hold units 280c includes the third sampling unit 281, the clamp switch 282, and the third output switch 285.

The second clamp hold units 280d are provided on the vertical transfer lines 239 (239b) in the even numbered columns. The second clamp hold units 280d sample the imaging signals subjected to photoelectric conversion in each of the unit pixels 230 and then output the sampled imaging signals to the amplifier 290. The second clamp hold unit 280a includes the third sampling unit 281a, the clamp switch 282a, and the third output switch 285a.

Operation of the Imaging Unit

Figure 8:
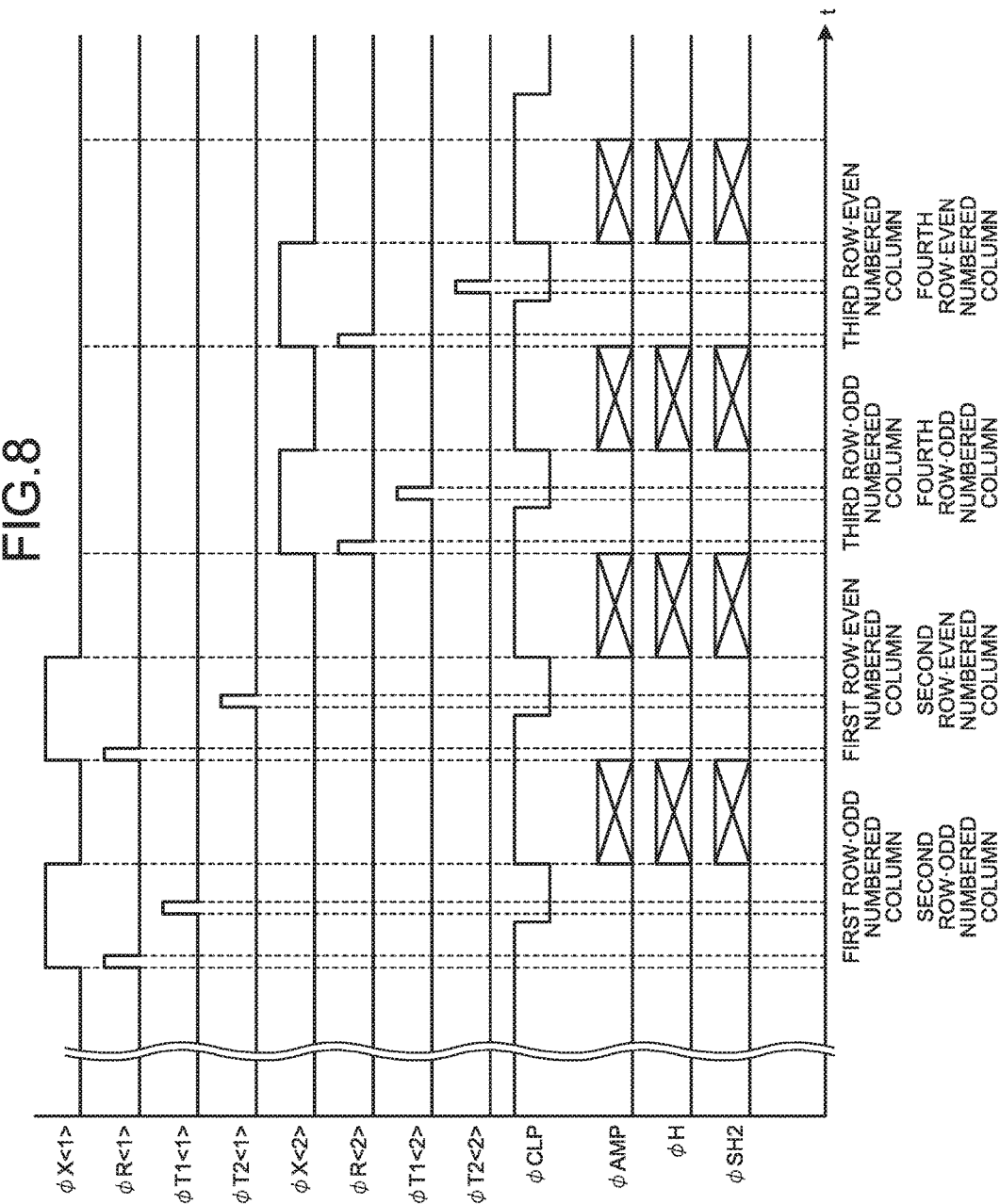
FIG. 8 is a timing chart illustrating a driving timing of an imaging unit according to the third embodiment.

In the following, a driving timing of the imaging unit 20 will be described. FIG. 8 is a timing chart illustrating a driving timing of the imaging unit 20 according to the third embodiment. FIG. 8 illustrates the timing of, in the order from the top, the row selection pulse φX<1>, the driving pulse φR<1>, the driving pulse φT1<1>, the driving pulse φT2<1>, the row selection pulse φX<2>, the driving pulse φR<2>, the driving pulse φT1<2>, the driving pulse φT2<2>, a driving pulse φCLP, the driving pulse φAMP, the column selection pulse φH, and the driving pulse φSH2.

As illustrated in FIG. 8, first, while maintaining the driving pulse φCLP in the on state, the timing generating unit 25 sets the row selection pulse φX<1> and the driving pulse φR<1> to the on state (High). Consequently, each of the charge voltage converter reset units 236 in the first row and the second row enters the on state, emits the signal charge accumulated in each of the charge voltage converters 233 in the first row and the second row, and resets each of the charge voltage converters 233 in the first row and the second row to the predetermined electric potential.

Subsequently, the timing generating unit 25 sets the driving pulse φR<1> to the off state (Low), allows internal nodes 287 in the first clamp hold units 280c to clamp the noise signals input from the charge voltage converters 233 in the first row via the vertical transfer lines 239 (239a) and the third sampling unit 281, and allows an internal node 287a in the second clamp hold units 280d to clamp the noise signals input from the charge voltage converters 233 in the second row via the vertical transfer lines 239 (239b) and the third sampling units 281a. At this time, the timing generating unit 25 sets the driving pulse φAMP to the on state (High) and resets the input/output of the first operational amplifier 293 to the same electric potential.

Then, the timing generating unit 25 sets the driving pulse φCLP to the off state (Low) and sets the driving pulse φT1<1> to the on state (High). In this case, each of the transfer transistors 234 in the first row and the second row enters the on state due to the driving pulse φT1<1> being input to the gate from the timing generating unit 25 and transfers the signal charge from the photoelectric conversion elements 231 to the charge voltage converters 233 in each of the odd numbered columns in the first row and the second row. At this time, the pixel output switches 238 in the first row output the imaging signals subjected to charge voltage conversion by the charge voltage converters 233 from the pixel source follower transistors 237 to the vertical transfer lines 239 (239a), whereas the pixel output switches 238 in the second row outputs the imaging signals subjected to charge voltage conversion by the charge voltage converters 233 from the pixel source follower transistors 237 to the vertical transfer lines 239 (239b). Furthermore, each of the third sampling unit 281 performs noise removal of the imaging signals in the odd numbered columns in the first row output from the vertical transfer lines 239 (239a) and samples to the internal nodes 287 in the first clamp hold units 280c, whereas each of the third sampling units 281a performs noise removal of the imaging signals in the odd numbered columns in the second row output from the vertical transfer lines 239 (239b) and samples to the internal nodes 287a in the second clamp hold units 280d.

Then, the timing generating unit 25 sets the row selection pulse φX<1> to the off state (Low), sets the driving pulse φCLP to the on state (High), and sequentially repeats, for each column, the on/off operation of the driving pulse φAMP, the column selection pulse φH<M>, and the driving pulse φSH2. In this case, each of the third sampling units 281 transfers, when the column selection pulse φH<M> is in the on state, the sampled imaging signals in the odd numbered columns in the first row to the first horizontal transfer lines 259a and outputs the transferred imaging signals to the first operational amplifier 293. The fifth sampling unit 302 outputs the sampled imaging signals to the first output amplification unit 311a in accordance with the on/off operation of the fourth sampling switch 301. The first output amplification unit 311a externally outputs the imaging signals in the odd numbered columns in the first row input from the fifth sampling unit 302 (Vout1).

Furthermore, each of the third sampling units 281a transfers, when the column selection pulse φH<M> is the on state, the sampled imaging signals in the odd numbered columns in the second row to the second horizontal transfer line 260a and outputs the transferred imaging signals to the second operational amplifier 296. The sixth sampling unit 304 outputs the sampled imaging signals to the second output amplification unit 312a in accordance with the on/off operation of the fifth sampling switch 303. The second output amplification unit 312a externally outputs the imaging signals in the odd numbered columns in the second row input to the sixth sampling unit 304 (Vout2).

Subsequently, the timing generating unit 25 sets the row selection pulse φX<1> and the driving pulse φR<1> to the on state (High). Consequently, each of the charge voltage converter reset units 236 in the first row and the second row enters the on state, emits the signal charge accumulated in each of the charge voltage converters 233 in the first row and the second row, and resets each of the charge voltage converters 233 in the first row and the second row to the predetermined electric potential.

Then, the timing generating unit 25 sets the driving pulse φR<1> to the off state (Low), allows the internal nodes 287 in the first clamp hold units 280c to clamp the noise signals input from the charge voltage converters 233 in the first row via the vertical transfer lines 239 (239a) and the third sampling units 281, and allows the internal nodes 287a in the second clamp hold units 280d to clamp the noise signals input from the charge voltage converters 233 in the second row via the vertical transfer lines 239 (239b) and the third sampling units 281a. At this time, the timing generating unit 25 sets the driving pulse φAMP to the on state (High) and resets the input/output of the first operational amplifier 293 to the same electric potential.

Then, the timing generating unit 25 sets the driving pulse φCLP to the off state (Low) and completes the clamping of the noise signals input from the charge voltage converters 233 in the first row via the vertical transfer lines 239 (239a). The clamping of the noise signals input from the charge voltage converters 233 in the second row via the vertical transfer lines 239 (239b) has been completed.

Subsequently, the timing generating unit 25 sets the driving pulse T2<1> to the on state (High). In this case, each of the transfer transistors 235 in the first row and the second row enters the on state due to the driving pulse φT2<1> being input to the gate from the timing generating unit 25 and transfers the signal charge from the photoelectric conversion elements 232 in each of the even numbered columns in the first row and the second row to the charge voltage converters 233. At this time, the pixel output switches 238 in the first row output the imaging signals subjected to charge voltage conversion by the charge voltage converters 233 from the pixel source follower transistors 237 to the vertical transfer lines 239 (239a), whereas the pixel output switches 238 in the second row outputs the imaging signal subjected to charge voltage conversion by the charge voltage converters 233 from the pixel source follower transistors 237 to the vertical transfer lines 239 (239b). Furthermore, each of the third sampling units 281 performs noise removal of the imaging signals in the even numbered columns in the first row output from the vertical transfer lines 239 (239a) and samples to the internal nodes 287 in the first clamp hold units 280c, whereas each of the third sampling units 281a performs noise removal of the imaging signals in the even numbered columns in the second row output from the vertical transfer lines 239 (239b) and samples to the internal nodes 287a in the second clamp hold units 280d.

Subsequently, the timing generating unit 25 sets the row selection pulse φX<1> to the off state (Low), sets the driving pulse φCLP to the on state (High), and sequentially repeats, for each columns, the on/off operation of the driving pulse φAMP, the column selection pulse φH<M>, and the driving pulse φSH2. In this case, when the column selection pulse φH<M> is in the on state, each of the third sampling units 281 transfers the sampled imaging signals in the even numbered columns in the first row to the first horizontal transfer lines 259a and outputs the transferred imaging signals to the first operational amplifier 293. The fifth sampling unit 302 outputs, in accordance with the on/off operation of the fourth sampling switch 301, the sampled imaging signal to the first output amplification unit 311a. The first output amplification unit 311a outputs the imaging signal in the even numbered columns in the first row input from the fifth sampling unit 302 to an external unit (Vout1).

Furthermore, when the column selection pulse φH<M> is in the on state, each of the third sampling units 281a transfers the sampled imaging signal in the even numbered columns in the second row to the second horizontal transfer line 260a and outputs the transferred imaging signals to the second operational amplifier 296. The sixth sampling unit 304 outputs, in accordance with the on/off operation of the fifth sampling switch 303, the sampled imaging signals to the second output amplification unit 312a. The second output amplification unit 312a outputs the imaging signals in the even numbered columns in the second row input from the sixth sampling unit 304 to an external unit (Vout2).

Subsequently, the timing generating unit 25 performs on/off operation of the row selection pulse φX<2>, the driving pulse φR<2>, the driving pulse φT1<2>, the driving pulse φT2<2>, the driving pulse φCLP, the driving pulse φAMP, the column selection pulse φH, and the driving pulse φSH2. Consequently, after having output the imaging signals in the odd numbered columns in the third row and the fourth row to an external unit, the timing generating unit 25 allows the imaging signals in the even numbered columns to output outside.

In this way, by controlling each of the vertical scanning unit 241, the first clamp hold units 280c, the second clamp hold units 280d, the amplifier 290, and the sample hold unit 300, the timing generating unit 25 simultaneously and alternately outputs the imaging signals in the odd numbered columns and the even numbered columns from each of the plurality of the unit pixels 230 located in two different rows to an external unit.

According to the third embodiment described above, the timing generating unit 25 simultaneously drives the pixels in the plurality of rows adjacent in the row direction (vertical direction) and simultaneously (in parallel) outputs, to the first output amplification unit 311a and the second output amplification unit 312a, the plurality of imaging signals output from the pixels in these plurality of rows; therefore, the time needed to read the imaging signal from each of the unit pixels 230 may be reduced to half, and it is thus possible to implement a reduction in size and readout at high speed.

Fourth Embodiment

In the following, a fourth embodiment will be described. In an endoscope system according to the fourth embodiment, the configuration of the first chip is different from that described in the third embodiment. Specifically, the first chip according to the third embodiment includes a column amplifier in a clamp hold circuit. In a description below, the configuration of the first chip according to the fourth embodiment will be described and then the operation of the imaging unit according to the fourth embodiment will be described. Furthermore, components that are identical to those in the endoscope system 1 according to the third embodiment are assigned the same reference numerals and descriptions thereof will be omitted.

Configuration of the First Chip

Figure 9:
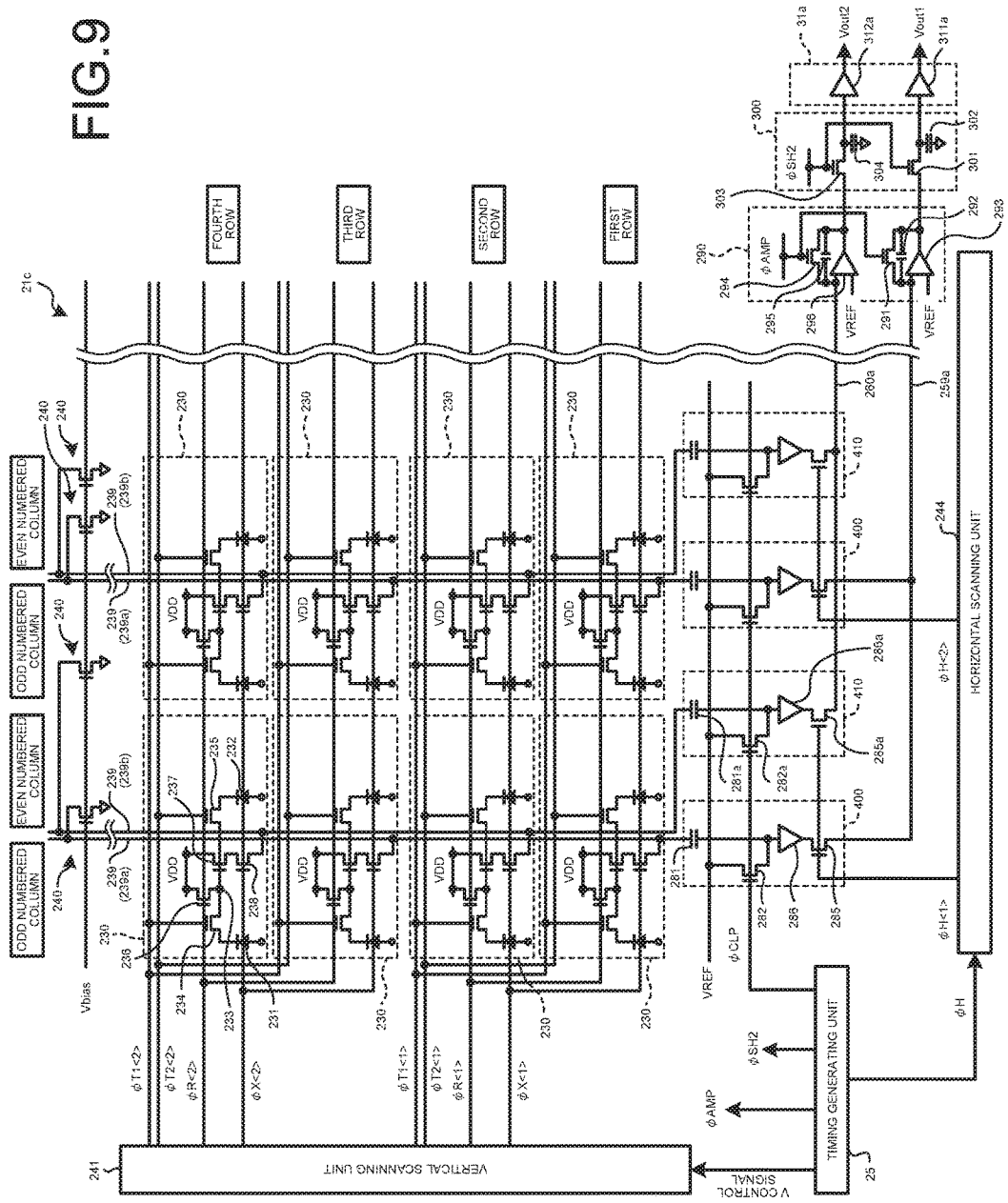
FIG. 9 is a circuit diagram illustrating the configuration of a first chip according to a fourth embodiment.

FIG. 9 is a circuit diagram illustrating the configuration of a first chip according to a fourth embodiment. Instead of the first clamp hold units 280c and the second clamp hold units 280d in the first chip 21b according to the third embodiment described above, a first chip 21c illustrated in FIG. 9 includes third clamp hold units 400 and fourth clamp hold units 410.

The third clamp hold units 400 are provided in the vertical transfer lines 239 (239a) in the odd numbered columns. Each of the third clamp hold units 400 samples the imaging signal subjected to photoelectric conversion by each of the unit pixels 230, amplifies the sampled imaging signal, and outputs the amplified imaging signal to the amplifier 290. Each of the third clamp hold unit 400 includes the third sampling unit 281, the clamp switch 282, the third output switch 285, and a column amplifier 286.

Each of the column amplifier 286 amplifies the imaging signals transferred from the vertical transfers line 239 (239a) in the odd numbered columns and outputs the amplified imaging signals to the amplifier 290.

The fourth clamp hold units 410 are provided in the vertical transfer lines 239 (239b) in the even numbered columns. Each of the fourth clamp hold units 410 samples the imaging signals subjected to photoelectric conversion by each of the unit pixels 230, amplifies the sampled imaging signals, and outputs the amplified imaging signals to the amplifier 290. Each of the fourth clamp hold unit 410 includes the third sampling unit 281a, the clamp switch 282a, the third output switch 285a, and a column amplifier 286a.

Each of the column amplifiers 286a amplifies the imaging signals transferred from the vertical transfer lines 239 (239b) in the even numbered columns and outputs the amplified imaging signals to the amplifier 290.

Operation of the Imaging Unit

Figure 10:
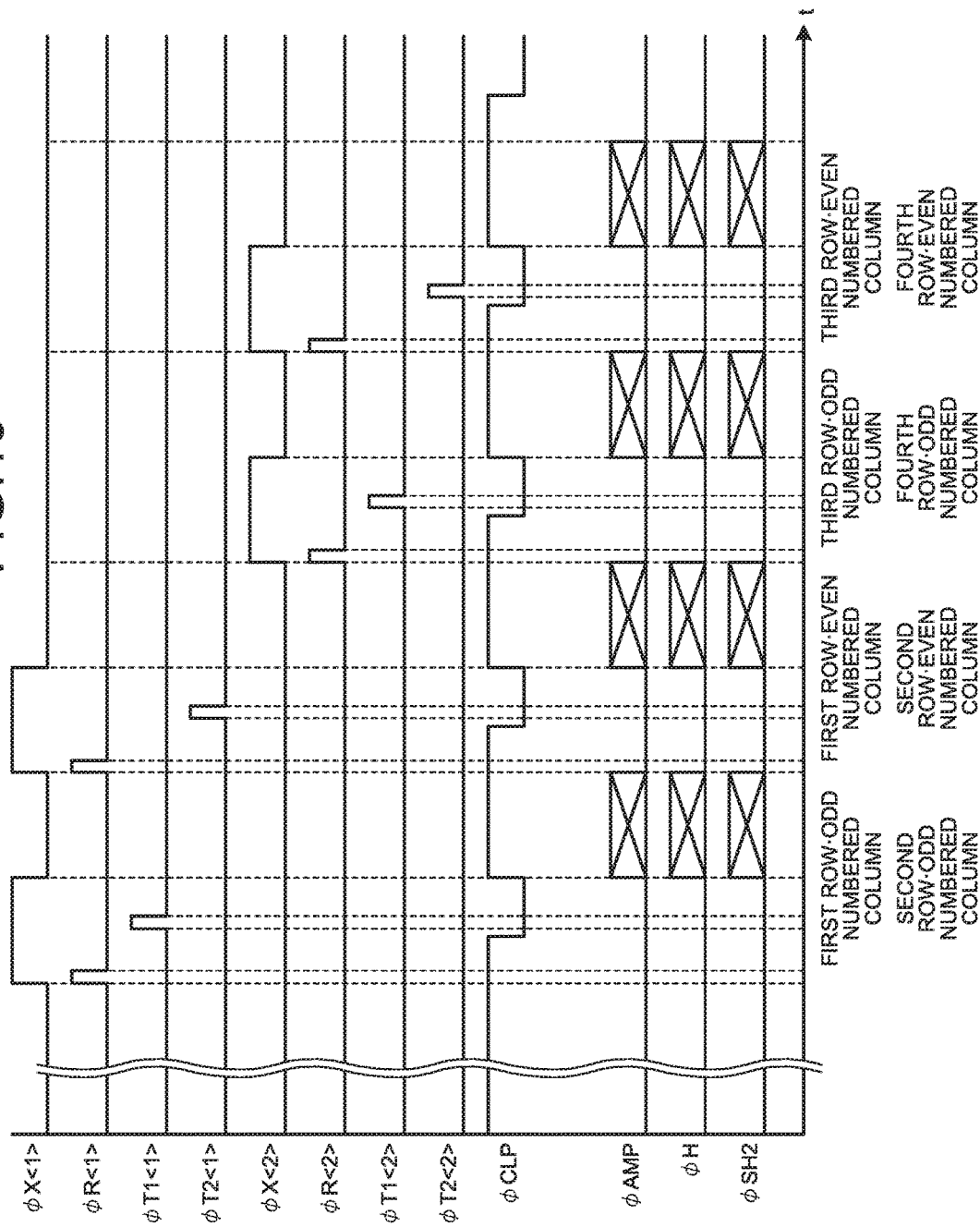
FIG. 10 is a timing chart illustrating a driving timing of an imaging unit according to the fourth embodiment.

In the following, a driving timing of the imaging unit 20 will be described. FIG. 10 is a timing chart illustrating a driving timing of the imaging unit 20 according to the fourth embodiment. FIG. 10 illustrates the timing of, in the order from the top, the row selection pulse φX<1>, the driving pulse φR<1>, the driving pulse φT1<1>, the driving pulse φT2<1>, the row selection pulse φX<2>, the driving pulse φR<2>, the driving pulse φT1<2>, the driving pulse φT2<2>, the driving pulse φCLP, the driving pulse φAMP, the column selection pulse φH, and the driving pulse φSH2.

As illustrated in FIG. 10, the timing generating unit 25 performs the same operation as that described the third embodiment above (see FIG. 8). Specifically, the timing generating unit 25 simultaneously and alternately outputs the imaging signals in the odd numbered columns and the even numbered columns from each of the plurality of the unit pixels 230 located in two different rows to an external unit while changing the on/off operation of the row selection pulse φX<1>, the driving pulse φR<1>, the driving pulse φT1<1>, the driving pulse φT2<1>, the row selection pulse φX<2>, the driving pulse φR<2>, the driving pulse φT1<2>, the driving pulse φT2<2>, the driving pulse φCLP, the driving pulse φAMP, the column selection pulse φH, and the driving pulse φSH2.

According to the fourth embodiment described above, the timing generating unit 25 simultaneously drives the pixels in the plurality of rows that are adjacent in the row direction (vertical direction) and simultaneously (in parallel) outputs the plurality of imaging signals output from the pixels in these plurality of rows to the first output amplification unit 311a and the second output amplification unit 312a; therefore, the time needed to read the imaging signal from each of the unit pixels 230 may be reduced to half, and it is thus possible to implement a reduction in size and readout at high speed.

Other Embodiments

Furthermore, in the embodiments, the endoscope inserted into a subject is used; however, for example, a capsule-type endoscope or an imaging device that captures a subject may also be used.

Furthermore, in the embodiments, the number of unit pixels that are allowed to share the vertical transfer line (the first transfer line) is two; however, the number of unit pixels is not limited to this. For example, shared pixels of 4 pixels or 8 pixels may also be used. In this case, the number of output amplifiers may also appropriately be provided in accordance with the number of shared pixels. Specifically, when four pixels are allowed to share a single vertical transfer line, the number of output amplifies to be provided is four (arrange four output channels).

In a description of the timing charts in the application, the relationship between before and after the processes performed at each Step is stated by using "first", "then", "subsequently", and the like; however, the order of the processes needed to implement the present disclosure is not uniquely determined by the descriptions above. Specifically, the order of the processes in the timing charts described in the application may also be changed as long as processes do not conflict with each other.

According to the present disclosure, an advantage is provided in that it is possible to implement both a reduction in size and readout at high speed.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image sensor comprising:
   a plurality of pixels arranged in a two-dimensional matrix and configured to receive light and generate imaging signals in accordance with an amount of received light;
   a plurality of first transfer lines configured to transfer the imaging signals of shared pixels of the plurality of pixels that are present in a plurality of different rows and share a single column transfer line for each predetermined number of pixels adjacent in a row direction and;
   a constant current source provided in each of the plurality of first transfer lines and configured to transfer the imaging signals output from the pixels to the first transfer lines;
   a plurality of output circuits configured to externally output the imaging signals transferred from the plurality of first transfer lines; and
   a processor comprising hardware, the processor being configured to simultaneously and externally output, from the plurality of output circuits, by simultaneously driving the plurality of shared pixels present in a same single column transfer line in the plurality of different rows, each of the plurality of imaging signals, which are output from the shared pixels and are present in the same column in the plurality of different rows, and externally output all of the imaging signals of the shared pixels present in the plurality of different rows same number of times as the predetermined number.

2. The image sensor according to claim 1, further comprising:
   noise removal circuits each provided in each of the plurality of first transfer lines and configured to remove a noise component of the imaging signals; and
   a plurality of second transfer lines configured to transfer the imaging signals from the first transfer lines to the output circuits via the noise removal circuits.

3. The image sensor according to claim 2, wherein
   the noise removal circuits include a plurality of sample hold capacitors, and
   the processor is further configured to allow the plurality of sample hold capacitors to simultaneously sample the imaging signals output from the pixels in the plurality of different rows and to simultaneously output the sampled imaging signals to the plurality of second transfer lines.

4. The image sensor according to claim 2, wherein
   each of the noise removal circuits includes
   a clamp capacitor, and
   a reset unit, and
   the processor is further configured to allow the clamp capacitor to simultaneously output, to the plurality of second transfer lines, the imaging signals output from the pixels in the plurality of different rows.

5. The image sensor according to claim 1, wherein the plurality of pixels share the first transfer lines in at least a row direction.

6. The image sensor according to claim 5, wherein the processor alternately outputs the imaging signals from the plurality of pixels in odd numbered columns and even numbered columns.

7. An endoscope comprising:
   an insertion portion configured to be inserted into a subject; and
   the image sensor according to claim 1, the image sensor being provided at a distal end side of the insertion portion.

8. An endoscope system comprising:
   the endoscope according to claim 7; and
   an image processor configured to convert the imaging signals to image signals.

* * * * *